(12) United States Patent
Schmitt

(10) Patent No.: US 8,366,442 B2
(45) Date of Patent: Feb. 5, 2013

(54) DENTAL APPARATUS FOR RADIOGRAPHIC AND NON-RADIOGRAPHIC IMAGING

(75) Inventor: Stephen M. Schmitt, San Antonio, TX (US)

(73) Assignee: Bankruptcy Estate of Voxelogix Corporation, San Antonio, TX (US)

( * ) Notice: Subject to any disclaimer, the term of this patent is extended or adjusted under 35 U.S.C. 154(b) by 732 days.

(21) Appl. No.: 11/674,956

(22) Filed: Feb. 14, 2007

(65) Prior Publication Data

US 2007/0190481 A1  Aug. 16, 2007

Related U.S. Application Data

(60) Provisional application No. 60/773,433, filed on Feb. 15, 2006.

(51) Int. Cl.
*A61C 19/04* (2006.01)
(52) U.S. Cl. ............... 433/73; 606/130; 378/170
(58) Field of Classification Search .......... 433/73; 606/130; 378/170, 204, 205
See application file for complete search history.

(56) References Cited

U.S. PATENT DOCUMENTS

| | | | |
|---|---|---|---|
| 4,208,794 A | 6/1980 | Gerber | |
| 4,226,592 A | 10/1980 | Schreinemakers | |
| 4,234,307 A * | 11/1980 | Draheim | 433/73 |
| 4,575,805 A | 3/1986 | Moermann et al. | |
| 4,615,678 A | 10/1986 | Moermann et al. | |
| 4,616,998 A * | 10/1986 | Wong | 433/73 |
| 4,766,704 A | 8/1988 | Brandestini et al. | |
| 4,795,345 A | 1/1989 | Ai et al. | |
| 4,837,732 A | 6/1989 | Brandestini et al. | |
| 4,859,181 A * | 8/1989 | Neumeyer | 433/69 |
| 4,901,737 A | 2/1990 | Toone | |
| 5,006,065 A | 4/1991 | Waysenson | |
| 5,090,047 A * | 2/1992 | Angotti et al. | 378/170 |
| 5,237,998 A * | 8/1993 | Duret et al. | 600/476 |
| 5,257,203 A | 10/1993 | Riley et al. | |
| 5,409,017 A | 4/1995 | Lowe | |
| 5,501,598 A | 3/1996 | Misch | |
| 5,527,182 A | 6/1996 | Willoughby | |
| 5,588,430 A * | 12/1996 | Bova et al. | 600/429 |
| 5,652,709 A | 7/1997 | Andersson et al. | |
| 5,662,476 A | 9/1997 | Ingber et al. | |
| 5,690,843 A | 11/1997 | Schmitt et al. | |
| 5,697,997 A | 12/1997 | Aronsson et al. | |
| 5,725,378 A | 3/1998 | Wang | |
| 5,733,126 A | 3/1998 | Andersson et al. | |

(Continued)

FOREIGN PATENT DOCUMENTS

EP  1561433 A1  8/2005
GB  2440267 A  1/2008

(Continued)

OTHER PUBLICATIONS

Schmitt, The 3rd Annual Eugene C. Gwaltney Manufacturing Symposium, "Rapid Prototyping for Product Development, Design, and Tooling: Making the New Technologies Pay Off for You" "Changing Peoples' Lives with RPM",Oct. 1-3, 1996, pp. 75-83 (10 pages).

(Continued)

*Primary Examiner* — Ralph Lewis
(74) *Attorney, Agent, or Firm* — Cox Smith Matthews Incorporated

(57) ABSTRACT

Methods and systems for making a computer model of a patient's jaws on the basis of digital information from computed tomography and non-radiographic digital imaging of the patient's teeth or dental casts of their teeth.

8 Claims, 18 Drawing Sheets

U.S. PATENT DOCUMENTS

| | | |
|---|---|---|
| 5,741,215 A | 4/1998 | D'Urso |
| 5,768,134 A | 6/1998 | Swaelens et al. |
| 5,779,477 A | 7/1998 | Boss |
| 5,800,174 A | 9/1998 | Andersson |
| 5,807,102 A | 9/1998 | Lang et al. |
| 5,816,810 A | 10/1998 | Antonson et al. |
| 5,823,778 A | 10/1998 | Schmitt et al. |
| 5,829,981 A | 11/1998 | Ziegler |
| 5,851,115 A | 12/1998 | Carlsson et al. |
| 5,857,853 A | 1/1999 | van Nifterick et al. |
| 5,868,138 A | 2/1999 | Halstrom |
| 5,871,358 A | 2/1999 | Ingber et al. |
| 5,880,962 A | 3/1999 | Andersson et al. |
| 5,938,446 A | 8/1999 | Andersson et al. |
| 5,951,289 A | 9/1999 | Kura et al. |
| 5,967,777 A | 10/1999 | Klein et al. |
| 5,975,893 A | 11/1999 | Chishti et al. |
| 5,989,029 A | 11/1999 | Osorio et al. |
| 5,993,214 A | 11/1999 | Persson |
| 6,015,289 A | 1/2000 | Andreiko et al. |
| 6,049,743 A | 4/2000 | Baba |
| 6,055,986 A | 5/2000 | Meade |
| 6,062,860 A | 5/2000 | Jorgenson |
| 6,066,274 A | 5/2000 | Antonson et al. |
| 6,082,995 A | 7/2000 | Wise |
| 6,126,445 A | 10/2000 | Willoughby |
| 6,149,433 A | 11/2000 | Ziegler et al. |
| 6,152,731 A | 11/2000 | Jordan et al. |
| 6,155,828 A | 12/2000 | Lazzara et al. |
| 6,159,010 A | 12/2000 | Rogers et al. |
| 6,168,435 B1 | 1/2001 | Beaty et al. |
| 6,186,790 B1 | 2/2001 | Karmaker et al. |
| 6,210,162 B1 | 4/2001 | Chishti et al. |
| 6,217,325 B1 | 4/2001 | Chishti et al. |
| 6,217,331 B1 | 4/2001 | Rogers et al. |
| 6,223,067 B1 * | 4/2001 | Vilsmeier et al. ............. 600/426 |
| 6,227,851 B1 | 5/2001 | Chishti et al. |
| 6,231,342 B1 | 5/2001 | Osorio et al. |
| 6,261,098 B1 | 7/2001 | Persson |
| 6,276,938 B1 | 8/2001 | Jorneus et al. |
| 6,283,752 B1 | 9/2001 | Kumar |
| 6,287,116 B2 | 9/2001 | Lazzara |
| 6,287,119 B1 | 9/2001 | van Nifterick et al. |
| 6,296,483 B1 * | 10/2001 | Champleboux ................. 433/75 |
| 6,302,686 B1 | 10/2001 | Chott et al. |
| 6,305,939 B1 | 10/2001 | Dawood |
| 6,319,006 B1 | 11/2001 | Scherer et al. |
| 6,322,359 B1 | 11/2001 | Jordan et al. |
| 6,343,930 B1 | 2/2002 | Beaty et al. |
| 6,354,836 B1 | 3/2002 | Panzera et al. |
| 6,361,318 B1 | 3/2002 | Back et al. |
| 6,382,975 B1 | 5/2002 | Poirier |
| 6,394,801 B2 | 5/2002 | Chishti et al. |
| 6,409,504 B1 | 6/2002 | Jones et al. |
| 6,419,489 B1 | 7/2002 | Jorneus et al. |
| 6,419,491 B1 | 7/2002 | Ricci et al. |
| 6,431,866 B2 | 8/2002 | Hurson |
| 6,463,344 B1 | 10/2002 | Pavloskaia et al. |
| 6,491,723 B1 | 12/2002 | Beaty |
| 6,505,625 B1 | 1/2003 | Uenishi |
| 6,524,106 B1 | 2/2003 | Ziegler |
| 6,530,375 B1 | 3/2003 | Cieslik, Jr. |
| 6,540,516 B1 | 4/2003 | Ziegler |
| 6,558,162 B1 | 5/2003 | Porter et al. |
| 6,582,931 B1 | 6/2003 | Kois et al. |
| 6,607,386 B1 | 8/2003 | Andersson et al. |
| 6,621,491 B1 * | 9/2003 | Baumrind et al. ............. 345/419 |
| 6,633,789 B1 | 10/2003 | Nikolskiy et al. |
| 6,640,150 B1 | 10/2003 | Persson et al. |
| 6,648,645 B1 | 11/2003 | MacDougald et al. |
| 6,652,765 B1 | 11/2003 | Beaty |
| 6,655,962 B1 | 12/2003 | Kennard |
| 6,665,570 B2 | 12/2003 | Pavloskaia et al. |
| 6,671,539 B2 * | 12/2003 | Gateno et al. ................. 600/426 |
| 6,705,863 B2 | 3/2004 | Phan et al. |
| 6,726,478 B1 | 4/2004 | Isiderio et al. |
| 6,767,208 B2 | 7/2004 | Kaza |
| 6,820,623 B2 | 11/2004 | Cook |
| 6,886,566 B2 | 5/2005 | Eubank |
| 6,935,861 B2 | 8/2005 | Lauciello |
| 6,947,038 B1 | 9/2005 | Anh et al. |
| 6,948,936 B2 | 9/2005 | Miller et al. |
| 7,047,978 B2 | 5/2006 | Zuk |
| 7,322,824 B2 | 1/2008 | Schmitt |
| 7,346,417 B2 * | 3/2008 | Luth et al. ..................... 700/117 |
| 2003/0065259 A1 | 4/2003 | Gateno et al. |
| 2004/0015176 A1 * | 1/2004 | Cosman ........................ 606/131 |
| 2004/0152036 A1 | 8/2004 | Abolfathi |
| 2004/0172150 A1 | 9/2004 | Perot et al. |
| 2004/0229185 A1 | 11/2004 | Knopp |
| 2005/0084144 A1 | 4/2005 | Feldman |
| 2005/0089822 A1 | 4/2005 | Geng |
| 2005/0106528 A1 | 5/2005 | Abolfathi et al. |
| 2005/0117693 A1 * | 6/2005 | Miyano ............................ 378/4 |
| 2005/0136371 A1 | 6/2005 | Abolfathi et al. |
| 2005/0153257 A1 | 7/2005 | Durbin et al. |
| 2005/0163342 A1 * | 7/2005 | Persky .......................... 382/103 |
| 2005/0170311 A1 | 8/2005 | Tardieu et al. |
| 2005/0244791 A1 | 11/2005 | Davis et al. |
| 2005/0271996 A1 | 12/2005 | Sporbert et al. |
| 2006/0040236 A1 | 2/2006 | Schmitt |
| 2006/0068355 A1 | 3/2006 | Schultz |
| 2006/0111806 A1 | 5/2006 | Kraemer et al. |
| 2006/0263738 A1 | 11/2006 | Kuo |
| 2007/0031791 A1 | 2/2007 | Cinader, Jr. et al. |
| 2007/0118243 A1 | 5/2007 | Schroeder et al. |
| 2007/0134625 A1 | 6/2007 | Leu et al. |
| 2007/0190492 A1 | 8/2007 | Schmitt |
| 2008/0020350 A1 | 1/2008 | Matov et al. |
| 2008/0032257 A1 * | 2/2008 | Muckler .......................... 433/75 |
| 2008/0064008 A1 | 3/2008 | Schmitt |
| 2008/0085489 A1 | 4/2008 | Schmitt |

FOREIGN PATENT DOCUMENTS

| | | |
|---|---|---|
| WO | WO9528688 | 10/1995 |
| WO | WO9932045 | 7/1999 |
| WO | WO2006009747 A1 | 1/2006 |
| WO | 2006031096 A1 | 3/2006 |
| WO | 2006096558 A2 | 9/2006 |
| WO | 2007079142 A2 | 7/2007 |
| WO | 2007084589 A2 | 7/2007 |
| WO | 2007084727 A1 | 7/2007 |
| WO | 2007130574 A1 | 11/2007 |
| WO | PCTUS07067424 | 1/2008 |
| WO | WO2007127804 A3 | 2/2008 |
| WO | PCT07062171 | 3/2008 |
| WO | PCTUS2007062171 | 8/2008 |

OTHER PUBLICATIONS

Schmitt, The 4th Annual Eugene C. Gwaltney Manufacturing Symposium, "Rapid Prototyping and Manufacturing: Applications in Product Development, Design and Tooling", "Changing Lives with RP", Georgia Institute of Technology, Oct. 1-2, 1997 pp. 21-26 (7 pages).

Leu, et al., U.S. Appl. No. 60/748,787, Computer Aided Dental Bar Design, filed Dec. 9, 2005 (97 pages).

Bisler, et al., "The Virtual Articulator—Applying VR Technologies to Dentistry", Proceedings of the Sixth International Conference on Information Visualisation, IEEE Computer Society, 2002 (3 pages).

Üşümez, et al., "Inclinometer Method for Recording and Transferring Natural Head Position in Cephalometrics", American Journal of Orthodontics and Dentofacial Orthopedics, vol. 120, No. 6, Dec. 2001 pp. 664-670 (7 pages).

Kordaβ, et al., "The Virtual Articulator in Dentistry: Concept and Development", The Dental Clinics of North America, 46, 2002, pp. 493-506 (14 pages).

Murphy, et al., "The Development of Instrumentation for the Dynamic Measurement of Changing Head Posture", American Journal of Orthodontics and Dentofacial Orthopedics, vol. 99, No. 6, Jun. 1991, pp. 520-526 (7 pages).

Usumez, et al., "Effect of Complete Dentures on Dynamic Measurement of Changing Head Position: A Pilot Study", The Journal of Prosthetic Dentistry, vol. 90, No. 4, Oct. 2003, pp. 394-440 (7 pages).

Üşümez, et al., "Reproducibility of Natural Head Position Measured with an Inclinometer", American Journal of Orthodontics and Dentofacial Orthopedics, vol. 123, No. 4, Apr. 2003, pp. 451-454 (4 pages).

Delli, "Automated Design and Fabrication of Dental Bar", University of Missouri-Rolla, Nov. 17, 2006 (23 pages).

Leu, et al., "Computer-Automated Dental Bar Design", Technology/Business Opportunity, University of Missouri-Rolla, no date (2 pages).

Gawate, "Dental Bar Design (Thesis)", University of Missouri, Published 2005 (67 pages).

Taylor, "Influence of Computerized Tomography Parameters on the Quality of Stereolithographic Models (Thesis)". The University of Texas Graduate School of Biomedical Sciences, Mar. 1999 (102 pages).

* cited by examiner

DENTAL APPARATUS FOR RADIOGRAPHIC AND NON-RADIOGRAPHIC IMAGING

This application claims priority to U.S. Provisional Application No. 60/773,433, filed Feb. 15, 2006, which is incorporated herein in its entirety by reference.

FIELD OF THE INVENTION

This disclosure relates to dental devices, systems, and methods, and more particularly to devices, systems, and methods for creating a computer model of a patient.

BACKGROUND

Dentists have found it useful to have a cast or replica of a patient's anatomy when analyzing and treating disorders of the jaws and making a dental prostheses. A dentist or prosthodontist will generally need a cast of an area of a patient's mouth where one or more teeth are missing and need replacement. This cast can be used in the dental lab to adjust and fit replacement teeth for proper size and shape, eliminating the need for the patient to be present. To create casts, an impression of the patient's upper and lower dental arch is first obtained. The impression is made by placing a curable material in an impression tray and positioning the tray over the patient's teeth and gums. After the material has cured it and the tray are removed from the mouth. The same process is used for both the upper and lower jaw. The actual dental cast is then made by pouring or placing a second curable material in the cured impression material. After the second material has cured the impression material is removed to produce the dental cast. Properly made, these dental casts provide an accurate physical replica of the patient's upper and lower teeth as well as the adjacent soft tissue. Modern impression materials can create casts that reproduce detail as fine as 10 microns.

A face bow may also be used to measure the distance and angulation of the upper arch in relation to the patient's temporal mandibular joint (TMJ). When used, the upper cast is mounted with the face bow in a device called an articulator such that the rotations centers approximate those of the patient. Other types of face bows record the position of the teeth in relation to the patient's "natural head position" or anatomic landmarks such as the ala of the nose and the tragus of the ear. Finally, many aesthetic aspects of the face may need to be mechanically recorded to have the proper information needed to plan aesthetic and functional dental prosthetics.

Casts are generally mounted in an articulator to reproduce the spatial relationship of the upper jaw to the lower and to approximate the movement of the patient's jaws. Frequently a specific jaw relationship is recorded in a wax bite. Wax is placed in the patient's mouth and the teeth are closed into the wax to record indentations of the teeth and to record the relative position of the upper and lower dental arch. Dental casts can then be placed into the wax bite and joined to the articulator such that the bite position can be reproduced by the articulator in the dental laboratory. The casts of a patient's teeth can also be mounted in an articulator by indexing the teeth in one arch into the teeth of the other in a position called maximum intercuspation. This eliminates the need for a wax bite. Many materials can be used instead of wax to make the bite record and many jaw positions may be recorded for specific dental applications.

Dental radiographs are also important in the diagnosis of aesthetic and functional dental problems. Orthodontists and oral surgeons use a lateral head film called a cephalometric radiograph to determine the length of the upper and lower jaws, the angulation of the teeth and the contour of the soft tissues. Many measurements can be made on these films to determine how the patient's anatomy is different from normal findings. Medical computed tomography (CT) has also been used extensively for evaluation of trauma and to plan for the placement of dental implants. CT has the advantage that the images are isometric and not distorted so that precise measurement of the bone and teeth can be made. New cone beam CT units are less expensive than conventional medical CT, have much lower radiation, are faster and allow the patient to be sitting upright in the "natural head position" for imaging. Unfortunately, dental radiographs and CT may produce scatter from metal fillings, gold crowns and other dental devices. This scatter may make the three-dimensional images of the teeth and occlusal surfaces of the teeth very imprecise and not of diagnostic quality. Even data from a patient without metal restorations may be not accurate enough for occlusal analysis when using CT as the only imaging process.

In recent years many patients not only want to have a healthy mouth and teeth but also want to improve their appearance with teeth that are in harmony with their face, lips, hair and eyes. Thus, it is desirable that a simplified system be developed to eliminate the need for a face bow and dental articulator. It would also be beneficial to create a precise virtual model of the patient's teeth and soft and hard tissues without scatter and at a lever of precision in the 10-20 micron range for occlusal analysis.

The devices, systems, and methods of the present disclosure overcomes one or more problems disclosed herein or in the art.

SUMMARY

In an exemplary aspect, this disclosure is directed to a method of creating a virtual computer model of a patient's upper jaw and mandible for kinematic analysis. The method may include acquiring non-radiographic data representing a digital model of the patient's upper and lower teeth and representing radiographic markers, and may include acquiring CT data representing the patient's upper jaw and mandible and representing radiographic markers. The CT data may be reformatted to generate a 3D CT image, and radiographic scatter from the CT image may be eliminated. The method also may include aligning the radiographic markers of the CT image with the radiographic markers of the digital model to move the digital model of the upper and lower teeth into a proper anatomic position in the CT image. Kinematics of the mandible relative to upper jaw on the CT image may be assessed.

In an exemplary aspect, the assessing kinematics may include determining a rotational center of the mandible of the CT image. In an exemplary aspect, the determining a rotational center of the mandible may include separating a mandible image from the CT image to allow for movement of the mandible image independent of the remaining CT image. In an exemplary aspect, the determining a rotational center may include determining an axis of rotation of the mandible using spatial positions of imaged condyles. In an exemplary aspect, the determining an axis of rotation may include selecting points with an input device on or around articulating surfaces of the imaged condyles. In an exemplary aspect, the method also may include rotating the mandible image about the axis. In an exemplary aspect, the method may include determining lateral and protrusive movements of the mandible image relative to the remaining CT image. In an exemplary aspect, the determining a rotational center may include recording opening, lateral, and protrusive movements of the patient's mandible with a digital recorder. In an exemplary aspect, the recording opening, lateral and protrusive movements may include associating sensors with a CT bite plate associated with the mandible and moving the patient's mandible while recording displacement of the sensors. In an exemplary aspect, the method may include saving data points along the rotational axis as digital data. In an exemplary aspect, the digital data may be ASCI text. In an exemplary aspect, the method may include moving the image of the mandible and teeth in relation to an upper jaw and head of the CT image.

In an exemplary aspect, the method may include evaluating aesthetic positions of soft and hard tissues taken in a natural position relative to a horizontal edge of a CT machine. In an exemplary aspect, the radiographic markers may be spheres and the aligning the radiographic markers may include aligning a specific point on the spheres. In an exemplary aspect, the aligning a specific point may include aligning the most superior point on the surface of each sphere.

In an exemplary aspect, the acquiring CT data may include acquiring CT data representing the patient's condyles. In an exemplary aspect, the method may include determining an orientation of the upper teeth of the CT image relative to the condyles of the CT image and their rotational centers. In an exemplary aspect, the method may include incorporating data sets representative of lower jaw movement of the CT image relative to the upper jaw of the CT image to produce motion of the lower jaw of the CT image.

In an exemplary aspect, eliminating radiographic scatter may include removing the upper and lower teeth from the CT image along with the radiographic scatter. In an exemplary aspect, the method may include including placing a CT bite plate between the upper and lower teeth in a patient's mouth, the CT bite plate having associated radiographic markers. In an exemplary aspect, the placing a CT bite plate may include orienting the CT bite plate so that the radiographic markers are above or below a plane of occlusion defined by the patient's upper and lower teeth. In an exemplary aspect, the acquiring non-radiographic data and the acquiring CT data may occur with the CT bite plate in the patient's mouth.

In an exemplary aspect, acquiring non-radiographic data includes forming an upper cast of the patient's upper teeth and forming a lower cast of the patient's lower teeth; and scanning the upper and lower casts. In an exemplary aspect, the scanning the upper and lower casts includes scanning with a contact digitizer. In an exemplary aspect, the acquiring non-radiographic data may include directly scanning the patient's upper and lower teeth in the patient's mouth. In an exemplary aspect, scanning the patient's upper and lower teeth may be accomplished with one of a photographic, light, laser, and holographic imaging system.

In another exemplary aspect, this disclosure is directed to a method of creating a virtual computer model of a portion of a patient's head. The method may include placing a CT bite plate between upper and lower teeth in the patient's mouth, the CT bite plate having associated radiographic markers, and may include imaging the teeth in the patient's mouth, without imaging casts of the teeth, using a non-radiographic imaging system to acquire non-radiographic data representing a digital model of the upper and lower teeth and the radiographic markers. The non-radiographic data may be formatted to generate a 3D digital model. CT data representing the patient's mandible and upper jaw and representing the radiographic markers may be acquired. The CT data may be formatted to a 3D CT image. Radiographic scatter from the CT image may be eliminated, and the radiographic markers of the CT image may be aligned with the radiographic markers of the digital model to move the image of the digital model into a proper anatomic position in the CT image.

In an exemplary aspect, the method may include assessing kinematics of a mandible of the head relative to upper jaw on the CT image. In an exemplary aspect, the assessing kinematics may include determining a rotational center of the mandible of the CT image. In an exemplary aspect, the determining a rotational center of a mandible may include separating the mandible of the CT image from the upper jaw of the CT image to allow for movement of the mandible image. In an exemplary aspect, the determining a rotational center may include determining an axis of rotation of the mandible using spatial position of condyles of the CT image. In an exemplary aspect, the determining an axis of rotation may include selecting points on or around articulating surfaces of the condyles of the CT image. In an exemplary aspect, the method may include rotating the mandible of the CT image about the axis of rotation. In an exemplary aspect, the method may comprise determining lateral and protrusive movements of the mandible of the CT image relative to the upper jaw of the CT image. In an exemplary aspect, the determining a rotational center may include recording opening, lateral, and protrusive movements of the patient's mandible with a digital recorder. In an exemplary aspect, the recording opening, lateral, and protrusive movements includes associating sensors with the CT bite plate and moving the mandible of the patient while recording displacement of the sensors. In an exemplary aspect, the method may include saving data points along the rotational axis as digital data. In an exemplary aspect, the digital data is ASCI text. In an exemplary aspect, the method may include moving the image of the mandible and lower teeth in relation to an image of an upper jaw and head.

In an exemplary aspect, the method may include evaluating aesthetic positions of soft and hard tissues taken in a natural position relative to the horizontal edge of a CT machine. In an exemplary aspect, the radiographic markers are spheres, and wherein the aligning the radiographic markings may include aligning a specific point on the spheres. In an exemplary aspect, the aligning a specific point includes aligning the most superior point on a surface of each sphere. In an exemplary aspect, the acquiring CT data includes acquiring CT data representing the patient's condyles. In an exemplary aspect, the method may include determining an orientation of the upper jaw of the CT image relative to the condyles of the CT image and their rotational centers. In an exemplary aspect, the method may include incorporating data sets representative of lower jaw movement of the CT image relative to the upper jaw of the CT image to produce motion of the lower jaw model of the CT image.

In an exemplary aspect, eliminating radiographic scatter may include removing upper and lower teeth from the CT image along with the radiographic scatter. In an exemplary aspect, the placing a CT bite plate may include orienting the CT bite plate so that the radiographic markers are above or below a plane of occlusion defined by the patient's upper and lower teeth. In an exemplary aspect, acquiring non-radiographic data is accomplished by scanning with one of a photographic, light, laser, and holographic imaging system.

In another exemplary aspect, this disclosure is directed to a dental apparatus, comprising a bite registration section formed of a radiolucent material and being configured to fit within a patient's mouth and mate with the patient's teeth, and also comprising a central forward projection extending from the bite registration section configured to extend between lips when the bite registration section is in the mouth. An exterior portion may be configured to reside outside the mouth, the exterior portion being attached to the central forward projection. The apparatus also may include at least three non-linear radiographic markers disposed on the exterior portion and having a radiographic density that makes them visible in the CT data.

In an exemplary aspect, at least one of the radiographic markers may be disposed on the exterior portion above or below a plane of occlusion formed by the patient's teeth. In an exemplary aspect, the radiographic markers may include a geometric shape that can be imaged with contact, light, laser, or holographic imaging techniques. In an exemplary aspect, the exterior portion may include first and second wings extending laterally relative to the central forward projection. In an exemplary aspect, at least two of the radiographic markers may be disposed on the first and second wings. In an exemplary aspect, the exterior portion includes a vertical portion extending above or below a plane of occlusion formed by the patient's teeth. In an exemplary aspect, the exterior portion also may include first and second wings extending laterally from the vertical portion. In an exemplary aspect, at least two of the radiographic markers may be disposed on the first and second wings. In an exemplary aspect, the first and second wings may extend laterally from the vertical portion and follow the contour of the face. In an exemplary aspect, at least one of the radiographic markers may be disposed on the vertical portion. In an exemplary aspect, the bite registration section is U-shaped. In an exemplary aspect, the apparatus may include bite registration material disposed in the bite registration section, the bite registration material being configured to record indentations of upper and lower teeth when the patient bites. In an exemplary aspect, the bite registration section may includes a bite surface.

In yet another exemplary aspect, this disclosure is directed to a method of creating a virtual computer model of a patient's head, the method may include placing a CT bite plate between upper and lower teeth in a patient's mouth, the CT bite plate having associated radiographic markers disposed to be above or below a plane of occlusion defined by the patient's upper and lower teeth. The method also may include scanning the patient's teeth and the CT bite plate with a non-radiographic imaging system to acquire non-radiographic data representing a digital model of the upper and lower teeth and the radiographic markers, and may include formatting the non-radiographic data to generate a 3D digital model. The method also may include scanning the patient's upper and lower teeth, mandible, upper jaw, and the CT bite plate with a CT machine to acquire CT data representing the patient's teeth and surrounding tissue and representing the radiographic markers. TT data may be formatted to a 3D CT image. Radiographic scatter and the upper and lower teeth may be eliminated from the CT image, and specific points on the radiographic markers of the CT image may be aligned with corresponding specific points on the radiographic markers of the digital model to move the image of the digital model into a proper anatomic position in the CT image. The mandible portion of the CT image may be separated from the upper jaw portion of the CT image to allow for movement of the mandible image independent of the upper jaw portion image. An axis of rotation of the mandible image corresponding to articulation points on the CT image may be determined. Lateral and protrusive movements of the mandible image relative to the upper jaw portion image also may be determined. The mandible of the CT image may be rotated about the axis of rotation.

In an exemplary aspect, the aligning specific points may include aligning the most superior point on a surface of the radiographic markers. In an exemplary aspect, the determining an axis of rotation and the determining lateral and protrusive movements may include recording opening, lateral, and protrusive movements of the patient's mandible with a digital recorder. In an exemplary aspect, the recording opening, lateral, and protrusive movements may include associating sensors with the CT bite plate and moving the mandible of the patient while recording displacement of the sensors. In an exemplary aspect, the method may include including saving data points along the determined axis of rotation as digital data. In an exemplary aspect, the digital data may be ASCI text.

In yet another exemplary aspect, this disclosure is directed to a system for creating a virtual computer model of a patient's upper jaw and mandible for kinematic analysis. The system may comprise means for acquiring non-radiographic data representing a digital model of the patient's upper and lower teeth and representing radiographic markers; and may comprise means for acquiring CT data representing the patient's upper jaw and mandible and representing radiographic markers. The system also may comprise means for reformatting the CT data to generate a 3D CT image, means for eliminating radiographic scatter from the CT image, means for aligning the radiographic markers of the CT image with the radiographic markers of the digital model to move the digital model of the upper and lower teeth into a proper anatomic position in the CT image, and means for assessing kinematics of the mandible relative to upper jaw on the CT image.

In an exemplary aspect, the means for assessing kinematics includes means for determining a rotational center of the mandible of the CT image. In an exemplary aspect, the means for determining a rotational center of the mandible may include means for separating a mandible image from the CT image to allow for movement of the mandible image independent of the remaining CT image. In an exemplary aspect, the means for determining a rotational center may include means for determining an axis of rotation of the mandible using spatial positions of imaged condyles. In an exemplary aspect, the means for determining an axis of rotation may include means for selecting points with an input device on or around articulating surfaces of the imaged condyles. In an exemplary aspect, the system may include means for rotating the mandible image about the axis. In an exemplary aspect, the system may include means for determining lateral and protrusive movements of the mandible image relative to the remaining CT image. In an exemplary aspect, the means for determining a rotational center includes means for recording opening, lateral, and protrusive movements of the patient's mandible with a digital recorder. In an exemplary aspect, the means for recording opening, lateral and protrusive movements includes means for associating sensors with a CT bite plate associated with the mandible and moving the patient's mandible while recording displacement of the sensors. In an exemplary aspect, the system includes means for saving data points along the rotational axis as digital data. In an exemplary aspect, the digital data is ASCI text. In an exemplary aspect, the system includes means for moving the image of the mandible and teeth in relation to an upper jaw and head of the CT image. In an exemplary aspect, the system may include means for evaluating aesthetic positions of soft and hard tissues taken in a natural position relative to a horizontal edge of a CT machine. In an exemplary aspect, the radiographic markers may be spheres and the means for aligning the radiographic markers may include means for aligning a specific point on the spheres. In an exemplary aspect, the means for aligning a specific point may include means for aligning the most superior point on the surface of each sphere.

In an exemplary aspect, the means for acquiring CT data may include means for acquiring CT data representing the patient's condyles. In an exemplary aspect, the system may include means for determining an orientation of the upper teeth of the CT image relative to the condyles of the CT image and their rotational centers. In an exemplary aspect, the system may include means for incorporating data sets representative of lower jaw movement of the CT image relative to the upper jaw of the CT image to produce motion of the lower jaw of the CT image.

In an exemplary aspect, the means for eliminating radiographic scatter may include removing the upper and lower teeth from the CT image along with the radiographic scatter. In an exemplary aspect, the system may include means for placing a CT bite plate between the upper and lower teeth in a patient's mouth, the CT bite plate having associated radiographic markers. In an exemplary aspect, the means for placing a CT bite plate includes means for orienting the CT bite plate so that the radiographic markers are above or below a plane of occlusion defined by the patient's upper and lower teeth. In an exemplary aspect, the means for acquiring non-radiographic data and the means for acquiring CT data operate with the CT bite plate in the patient's mouth. In an exemplary aspect, the means for acquiring non-radiographic data includes means for forming an upper cast of the patient's upper teeth and means for forming a lower cast of the patient's lower teeth, and means for scanning the upper and lower casts. In an exemplary aspect, the means for scanning the upper and lower casts includes a contact digitizer. In an exemplary aspect, the means for acquiring non-radiographic data includes means for directly scanning the patient's upper and lower teeth in the patient's mouth. In an exemplary aspect, the means for scanning the patient's upper and lower teeth is one of a photographic, light, laser, and holographic imaging system.

In yet another exemplary aspect, the present disclosure is directed to a system for creating a virtual computer model of a patient's head, comprising a bite plate disposable between teeth in a patient's mouth, the bite plate having associated radiographic markers, and comprising means for imaging the teeth in the patient's mouth, without imaging casts of the teeth, using a non-radiographic imaging system to acquire non-radiographic data representing a digital model of the upper and lower teeth and the radiographic markers. The system also may comprise means for formatting the non-radiographic data to generate a 3D digital model, and means for acquiring CT data representing the patient's mandible and upper jaw and representing the radiographic markers. The system also may comprise means for formatting the CT data to a 3D CT image, means for eliminating radiographic scatter from the CT image, and means for aligning the radiographic markers of the CT image with the radiographic markers of the digital model to move the image of the digital model into a proper anatomic position in the CT image.

In an exemplary aspect, the system may include means for assessing kinematics of a mandible of the head relative to upper jaw on the CT image. In an exemplary aspect, the means for assessing kinematics may include means for determining a rotational center of the mandible of the CT image. In an exemplary aspect, the means for determining a rotational center of a mandible includes means for separating the mandible of the CT image from the upper jaw of the CT image to allow for movement of the mandible image. In an exemplary aspect, the means for determining a rotational center includes means for determining an axis of rotation of the mandible using spatial position of condyles of the CT image. In an exemplary aspect, the means for determining an axis of rotation includes means for selecting points on or around articulating surfaces of the condyles of the CT image. In an exemplary aspect, the system may include means for rotating the mandible of the CT image about the axis of rotation. In an exemplary aspect, the system may further comprise means for determining lateral and protrusive movements of the mandible of the CT image relative to the upper jaw of the CT image. In an exemplary aspect, the means for determining a rotational center includes means for recording opening, lateral, and protrusive movements of the patient's mandible with a digital recorder. In an exemplary aspect, the means for recording opening, lateral, and protrusive movements includes means for associating sensors with the CT bite plate and moving the mandible of the patient while recording displacement of the sensors. In an exemplary aspect, the system may include means for saving data points along the rotational axis as digital data. In an exemplary aspect, the digital data is ASCI text. In an exemplary aspect, the system may include means for moving the image of the mandible and lower teeth in relation to an image of an upper jaw and head.

In an exemplary aspect, the system may include means for evaluating aesthetic positions of soft and hard tissues taken in a natural position relative to the horizontal edge of a CT machine. In an exemplary aspect, the radiographic markers are spheres, and wherein the means for aligning the radiographic markings may include means for aligning a specific point on the spheres. In an exemplary aspect, the means for aligning a specific point may include means for aligning the most superior point on a surface of each sphere. In an exemplary aspect, the means for acquiring CT data may include means for acquiring CT data representing the patient's condyles. In an exemplary aspect, the system may include means for determining an orientation of the upper jaw of the CT image relative to the condyles of the CT image and their rotational centers. In an exemplary aspect, the system may include means for incorporating data sets representative of lower jaw movement of the CT image relative to the upper jaw of the CT image to produce motion of the lower jaw model of the CT image. In an exemplary aspect, the means for eliminating radiographic scatter may include means for removing upper and lower teeth from the CT image along with the radiographic scatter. In an exemplary aspect, the bite plate may be configured so that the radiographic markers are above or below a plane of occlusion defined by the patient's upper and lower teeth. In an exemplary aspect, the means for acquiring non-radiographic data may be accomplished by scanning with one of a photographic, light, laser, and holographic imaging system.

In an exemplary aspect, this disclosure is directed to a method of creating a treatment plan for a dental patient. The method may comprise orienting the patient's head in a CT imaging system such that the position of the head is in a natural position relative to a horizontal reference, and scanning the patient's head with the CT imaging system to acquire CT data. The CT data may be reformatted to create a 3D soft tissue model of the soft tissues and to create a 3D hard tissue model of the hard tissues of the head. Aesthetic diagnostic evaluation may be performed using the soft tissue and hard tissue models of the patient's head in the natural position.

In an exemplary aspect, performing aesthetic diagnostic evaluation may include measuring spatial relationships between facial features on the hard tissue model and the soft tissue model in the natural position. In an exemplary aspect, the method may include placing a CT bite plate in the patient's mouth prior to scanning the patient's head. In an exemplary aspect, the horizontal reference is a horizontal edge of a detector of the CT imaging system. In an exemplary aspect, the orienting the patient's head may include instructing the patient to look at an object disposed relatively horizontally from the patient's head. In an exemplary aspect, the method may include rotating the model of the hard tissues. In an exemplary aspect, the method may include assessing kinematics of a mandible of the hard tissue model relative to the upper jaw on the hard tissue model. In an exemplary aspect, assessing kinematics may include determining a rotational center of the mandible of the hard tissue model. In an exemplary aspect, determining a rotational center of the mandible may include separating a mandible image from the hard tissue model to allow for movement of the mandible image independent of the remaining hard tissue model. In an exemplary aspect, the determining a rotational center may include determining an axis of rotation of the mandible using spatial positions of imaged condyles on the hard tissue model. In an exemplary aspect, the determining an axis of rotation may include selecting points with an input device on or around articulating surfaces of the imaged condyles. In an exemplary aspect, the method may include rotating the mandible image about the axis. In an exemplary aspect, the method may include determining lateral and protrusive movements of the mandible image relative to the remaining hard tissue model. In an exemplary aspect, the determining a rotational center includes recording opening, lateral, and protrusive movements of the patient's actual mandible with a digital recorder. In an exemplary aspect, the recording opening, lateral and protrusive movements may include associating sensors with a CT bite plate associated with the mandible and moving the patient's mandible while recording displacement of the sensors. In an exemplary aspect, the method may include saving data points along the rotational axis as digital data. In an exemplary aspect, the digital data is ASCI text. In an exemplary aspect, the method may include moving the image of the mandible in relation to an upper jaw and head of the hard tissue model.

In yet another exemplary aspect, the present disclosure is directed to a method of reproducing in a computer model actual movement of a mandible relative to an upper jaw of a patient. The method may include attaching a first sensor to the patient's mandible and detecting the position of the first sensor relative to the upper jaw with a second sensor associated with the head of the patient. It also may include displacing the patient's mandible relative to the upper jaw in an open and close direction, and recording first digital data representing the location of the upper jaw and mandible during the displacement of the patient's mandible in the open and close direction. It further may include displacing the patient's mandible relative to the upper jaw in a lateral direction and in a protrusive direction and recording second digital data representing the lateral and protrusive locations of the upper jaw and mandible during the displacement of the mandible in the lateral and protrusive directions. The method also may include determining a rotational center of the mandible, recording the rotational center as third digital data, and introducing the first, second, and third digital data to the computer model. Movement of the mandible in the computer model may be reproduced using the first, second, and third digital data.

In an exemplary aspect, the determining a rotational center of the mandible includes determining an axis of rotation of the mandible using spatial positions of imaged condyles. In an exemplary aspect, the determining an axis of rotation includes selecting points with an input device on or around articulating surfaces of the imaged condyles. In an exemplary aspect, the method may include rotating the mandible image about the axis. In an exemplary aspect, the method may include saving data points along the rotational axis as digital data. In an exemplary aspect, the digital data is recorded as ASCI Text.

In another exemplary aspect, the present disclosure is directed to a method of creating a treatment plan for a dental patient. The method may comprise placing a CT bite plate in the patient's mouth prior to scanning the patient's head, the CT bite plate having radiographic markers disposed thereon. The method also may comprise orienting the patient's head in a CT imaging system such that the position of the head is in a natural position relative to a horizontal reference; scanning the patient's head with the CT imaging system to acquire CT data, and also may comprise reformatting the CT data to create a 3D soft tissue model of the soft tissues and to create a 3D hard tissue model of the hard tissues of the head. The method also may comprise determining a rotational center of the mandible of the hard tissue model by separating a mandible image from the hard tissue model to allow for movement of the mandible image independent of the remaining hard tissue model. Aesthetic diagnostic evaluation may be performed, including measuring spatial relationships between facial features on the hard tissue model and the soft tissue model in the natural position, and determining a treatment plan for the patient based upon the rotational center of the mandible and the measured spatial relationships.

In an exemplary aspect, the horizontal reference is a horizontal edge of a detector of the CT imaging system. In an exemplary aspect, the orienting the patient's head includes instructing the patient to look at an object disposed relatively horizontally from the patient's head. In an exemplary aspect, the method may include assessing kinematics of the mandible of the hard tissue model relative to the upper jaw on the hard tissue model. In an exemplary aspect, the determining a rotational center may include determining an axis of rotation of the mandible using spatial positions of imaged condyles. In an exemplary aspect, the determining an axis of rotation may include selecting points with an input device on or around articulating surfaces of the imaged condyles. In an exemplary aspect, the method may include rotating the mandible image about the axis. In an exemplary aspect, the method may include determining lateral and protrusive movements of the mandible image relative to the remaining hard tissue model. In an exemplary aspect, the determining a rotational center may include recording opening, lateral, and protrusive movements of the patient's actual mandible with a digital recorder. In an exemplary aspect, the recording opening, lateral and protrusive movements may include associating sensors with the CT bite plate and moving the patient's mandible while recording displacement of the sensors. In an exemplary aspect, the method may include saving data points along the rotational axis as digital data. In an exemplary aspect, the digital data is ASCI text. In an exemplary aspect, the method may include moving the image of the mandible in relation to an upper jaw and head of the hard tissue model.

Further aspects, forms, embodiments, objects, features, benefits, and advantages of the present invention shall become apparent from the detailed drawings and descriptions provided herein.

DETAILED DESCRIPTION

Figure 1:
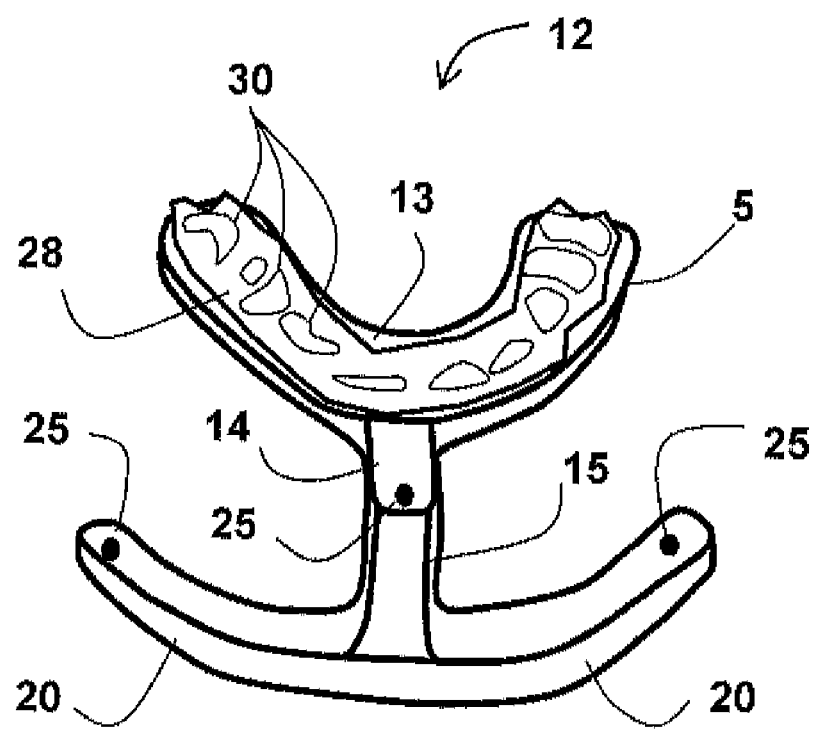
FIG. 1 is a schematic view of an exemplary CT bite plate with bite registration material.

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Briefly stated, the invention is directed to a system, including apparatuses and methods, for orienting a patient's jaws, teeth soft tissue and supporting bone in a virtual computer model that reduces radiographic scatter, and eliminates the use of a face bow and mechanical articulator. In addition, CT data about the patient may be recorded such that the aesthetic position of the teeth, head, eyes, lips, ears and any other soft or hard tissue can be measured and recorded in relation to "natural head position" such that the data will represent the patient with normal head posture. Once created, the virtual computer model can also incorporate movement from a digital recording device such as the ARCUSdigma (KaVo Company) or any other digital recorder that measures lower jaw movement in relation to the maxillary teeth or maxillae. This virtual model can also create motion of the lower jaw in relation to the upper by using known standard angulations and approximations for the distance of the teeth from the rotational centers. Many semi-adjustable mechanical articulators are designed with similar average or standard settings.

A radiolucent CT bite plate may be used to record the position of the patient's teeth during CT imaging. The CT bite plate may be rigid and may include three or more non-linear radiographic markers imbedded in it. Bite registration material may be placed on the bite plate and the patient may bite into the material to record a specific jaw position. The bite plate may include an extension that projects through the lips and extends vertically away from the plane of occlusion and laterally around and away from the soft tissues of the face. The radiographic markers can be detected in the CT image but do not create scatter. The bite plate may then be used at the time of CT imaging to position the patient's teeth and jaws in a known relationship and to create radiographic images of the position of the bite plate in the CT scan. If a cone beam machine is used that allows the patient to sit upright, the head is positioned in natural head position or any other diagnostic position that is required for aesthetic and diagnostic analysis. The resulting image will have the position of the teeth and soft tissues recorded in relation to horizontal.

A digital data set may also be made of the patient's teeth and soft tissues using non-radiographic imaging of the teeth and tissues directly in the mouth with photographic, light, laser, holographic or any other imaging system that will record the teeth with an acceptable precision. An alternative process is to make conventional dental impressions of the upper and lower jaws and to then image the dental casts made from the impressions. If dental casts are made, the casts can be scanned with contact digitizing in addition to the above mentioned processes. For data sets made from dental casts, the jaw position may be recorded using the CT bite plate. If the teeth are scanned directly in the mouth, the relationship of the upper and lower jaw may be recorded by imaging the surfaces of the teeth in both arches at the same time with the patient biting into the CT bit plate. Alternatively, the arches may be separately scanned.

If dental casts of the upper and lower jaws are made, a preferred embodiment is to use a cast holder to record the position of the upper and lower dental cast in relation to the CT bite plate. The casts may be joined to mounting plates that record their relationship to the CT bite plate and the cast holder. The mounting plates may include magnetic or mechanical fixation systems that join the mounting plates to receivers on the cast holder. Casts can then be removed from the cast holder in a known spatial relationship to the receiver. The casts can then be moved to the imaging system for imaging. Since the data sets for the upper and lower dental cast are known in relation to the mounting plates and cast holder, data sets from the upper and lower casts can be moved in computer space such that the same three-dimensional orientation exists in computer space as existed when the bite plate was in the mouth. This creates an accurate virtual computer model of the upper teeth and tissues in relation to the lower teeth and tissues in a specific static orientation. The computer models and fixation device should record the form of the teeth and the positional relation of each data set to a high level of precision since patients can feel an object 12 microns thick between their teeth.

The computer model of the upper and lower jaws just described can be very precise but it does not have information about the shape of the bone supporting the teeth or the position of nerve canals and other information obtained using CT. The present invention solves this problem by imaging the patient's head and jaws with CT using the CT bite plate. The CT data set may be made with the patient biting into the CT bite plate and may orient the data set to three radiographic markers that allow the information to be moved in computer space such that three dimensional data sets for the dental casts or teeth made using non-radiographic techniques are in the same orientation as the CT data set. Finally, the patient's head can be positioned during the CT scan such that a normal position (natural head position) or any other diagnostic position can be recorded. This will allow for the precise analysis of the orientation of the teeth to the eyes, face, lips, ears, horizontal or any other diagnostic reference point recorded during the scan.

The computer model made using the described invention creates a precise static model of the patient in a specific jaw position. Movement of the computer model can be created by using data from the CT scan to determine the orientation of the upper teeth to the condyles and rotational centers. This is commonly done in the dental art by using a face bow to approximate the position of the condyles using the ear hole opening as a guide. The actual condyles imaged in the CT can also be used and information about the shape of the condylar fossae may also be a good approximation of movement. This invention also provides for the incorporation of data sets from commercial digital recording devices. These devices record movement of the lower jaw in relation to the upper jaw and since a static starting point has been recorded with the CT bite plate, it is a simple process to produce motion of the lower jaw model from that point in virtual computer space.

Figure 5:
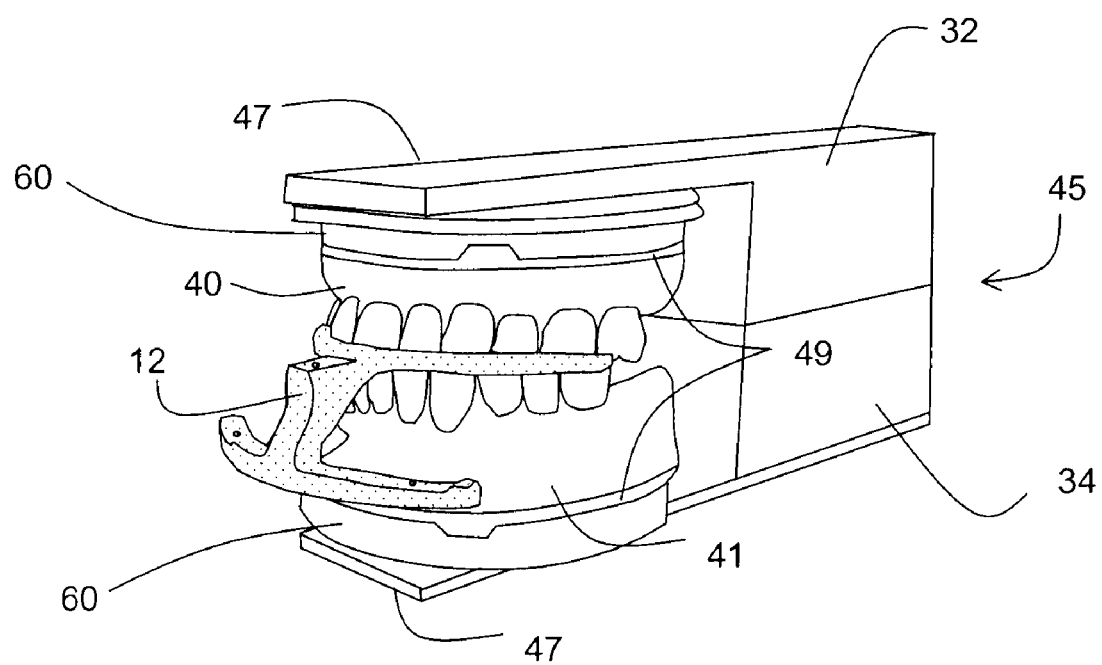
FIG. 5 illustrates an exemplary cast holding device and exemplary reference plates.
Figure 6:
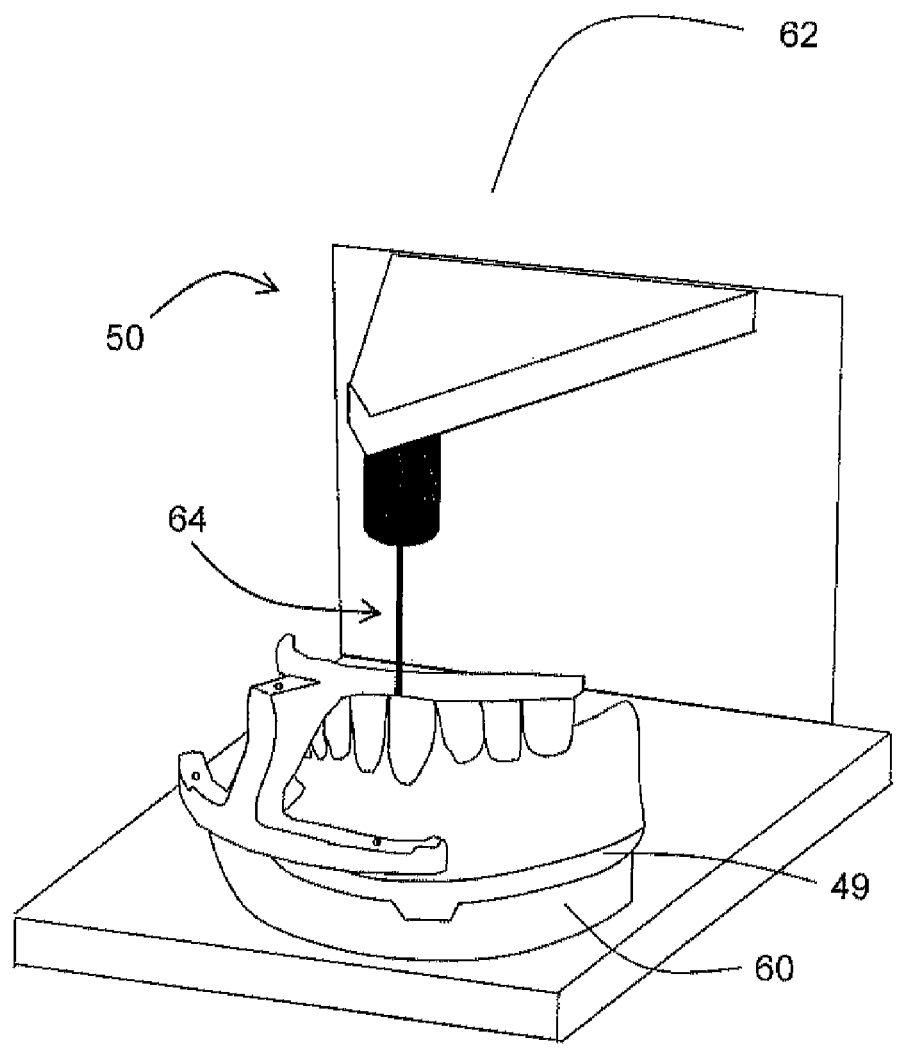
FIG. 6 is a schematic of an exemplary non-radiographic imaging system.

Turning now to the figures, FIG. 1 illustrates an exemplary CT bite plate assembly 12 that may be used when capturing a CT of a patient's teeth. The bite plate assembly 12 may include a U-shaped rigid section 5 attached to a thin bite surface 13 made of a radiolucent material that mates with the patient's teeth and yet requires minimal opening of the jaws. The bite surface 13 may include a central forward projection 14 that extends between the lips when the assembly 12 is placed in a patient's mouth. The forward projection 14 may be joined to a vertical portion 15 that, in some embodiments, extends above or below the plane of occlusion. Wings 20 extend laterally from the vertical portion and follow the contour of the face but are spaced apart from the face and thus do not contact it. In this exemplary embodiment, three or more non-linear radiographic markers 25 are attached to the vertical and wing portions of the CT bite plate. These markers 25 have a radiographic density that makes them visible in the CT data and also have a geometric shape that can be imaged with contact, light, laser, or holographic imaging techniques. Bite registration material 28 may be used to record the indentations 30 of the upper and lower teeth when the patient bites into the CT bite plate assembly 12. As shown in FIG. 1, in some embodiments, the radiographic markers 25 may be located forward of the bite registration section 5. As shown in FIGS. 1, 5, and 6, in some embodiments, the bite registration section 5, forward projection 14, vertical portion 15, and wings 20 may be a monolithic structure. As shown in FIGS. 1, 2, 5, 6, 8A, 12, and 13, in some embodiments, wings 20 may be curved and may extend laterally and rearwardly from vertical portion 15 at an elevation below bite surface 13 (for example, proximal to the patient's chin) and may terminate at a peripheral location forward of the patient's mandibular condyles 72 (see FIG. 10), such as a location proximal to the patient's teeth. In some embodiments, the lateral span of wings 20 may be less than the width of the patient's face.

In some examples, except for the radiographic markers, the CT bite plate assembly is formed entirely of a substantially radiolucent material. Accordingly, as described below, images captured by a CT machine may clearly display the radiographic markers 25 while less clearly showing the CT bite plate assembly 12. In some embodiments, the radiographic markers 25 are disposed above or below the plane of occlusion formed by the upper and lower teeth. This may enable better imaging and may reduce the chance of the image of the radiographic markers 25 being skewed by its position relative to other radiographic materials in the mouth, such as dental treatment devices, including fillings, crowns, and braces, among others. The exemplary CT bite plate assembly 12 in FIG. 2 includes three radiographic markers. In yet other exemplary embodiments, the CT bite plate assembly may include two or more than four radiographic markers 25 that are disposed above or below the plane of occlusion.

Figure 2:
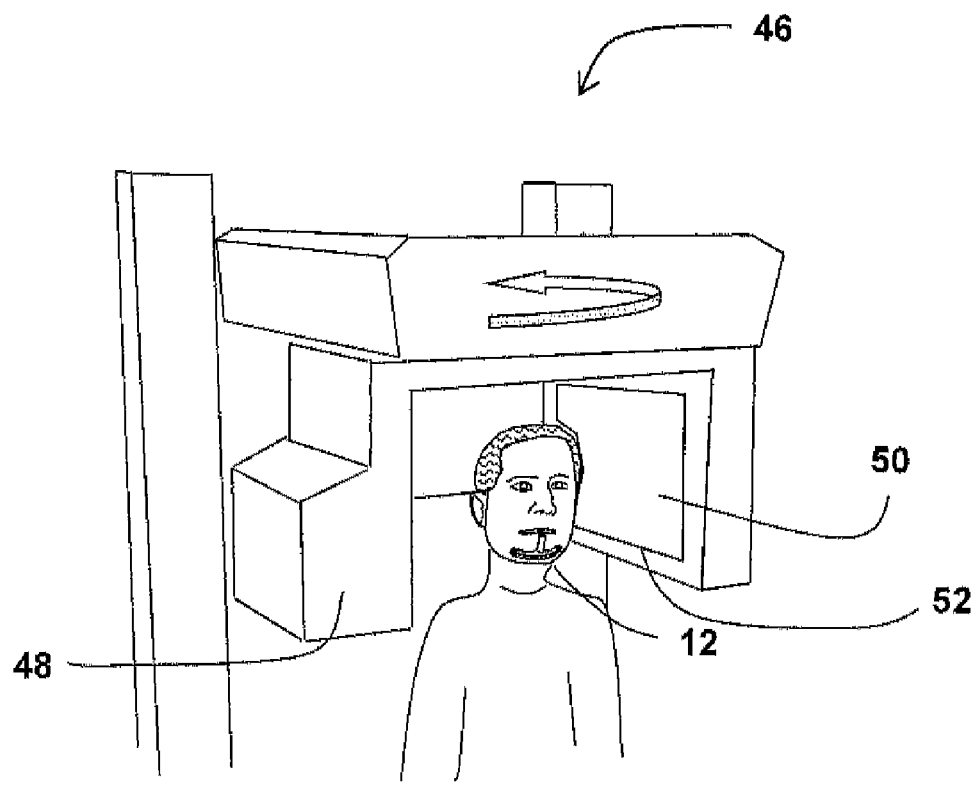
FIG. 2 is a schematic view illustrating the positioning of a patient in a cone beam CT machine with the CT bite plate in the mouth.

FIG. 2 illustrates the CT bite plate assembly 12 placed in a patient's mouth and the patient positioned in a CT machine 46. The x ray source 48 projects radiation across the patient's head and is detected on a rectangular shaped sensor or detector 50. In this example, the patient's head is positioned in a natural posture in relation to the floor and to the horizontal edge of the detector 52. As the x ray source 48 and detector 50 rotate around the patient, the normal head posture may be recorded in the scan data. In some exemplary embodiments, the CT machine is a cone beam CT unit.

Conventional scanning operations may include orienting the patient's head in a position that is not the natural position. The term "natural position," as used herein, refers to a forward facing person appearing as they would in a social setting. Because the image itself includes no reference points, in order to capture the teeth in a known, reproducable orientation, the patient may be required to hold his head or bend his neck in an unnatural position during capturing. Then, the physician can make a treatment plan based on the known orientation. These positions, while still allowing capturing of desired spatial relationships between facial features, may not create a realistic image of the patient's natural posture because the head was not in a natural position during scanning, and there is no reference that later tells the physician when the head image is oriented in the natural position. Accordingly, using the captured images to create treatment plans that involve jaw and teeth displacement may consider the patient's appearance in an un-natural posture, providing an appearance that often differs from the patient's natural appearance.

In contrast, scanning the patient's head in a natural position or posture in relation to the floor or in relation to the horizontal edge of the detector may be advantageous when the captured images are used to create a treatment plan affecting aesthetics. Because the scan is taken with the head in a natural position, the aesthetic position of the teeth, head, eyes, lips, ears, and any other soft or hard tissue can be measured and recorded as the patient would appear to others in social settings, instead of with his or her head tilted back or otherwise placed in an unnatural position. Thus, the natural position of the head is known relative to the horizontal edge of the detector. While developing a treatment plan, the physician can return the image of the head to the natural position for analysis. Further, because the natural position of the head image is known relative to the horizontal edge of the detector, the image still may be manipulated to positions other than the natural position if desired.

Thus, unlike prior systems that capture images in an unnatural position relative to a fixed reference point, the system disclosed herein may capture images in a natural position relative to a fixed reference point, such as a horizontal edge of the detector. A physician then, while manipulating a CT image, can always return the image to the reference point to return to the natural position.

Figure 3:
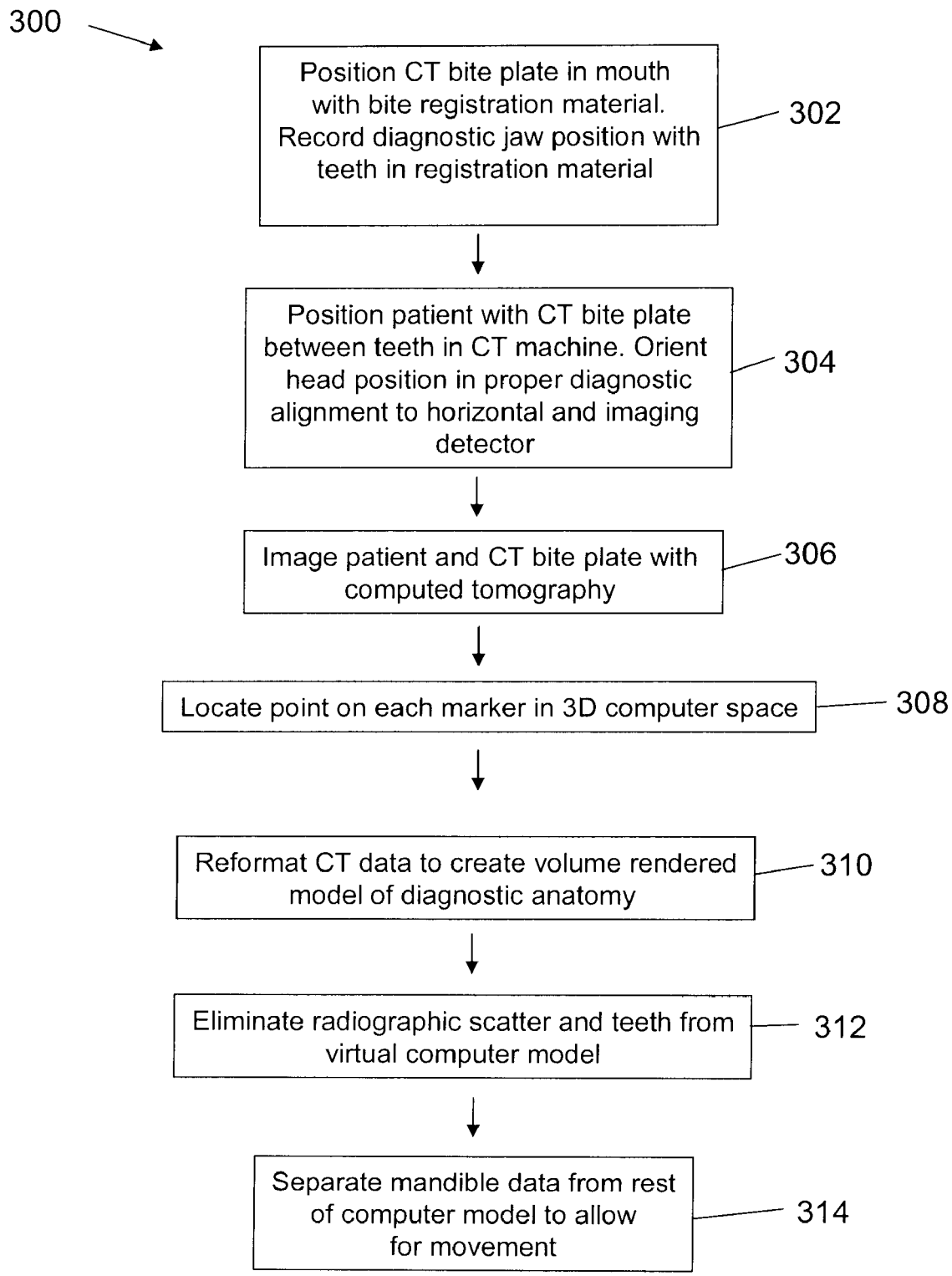
FIG. 3 is a flow chart showing an exemplary process for CT imaging the patient with the CT bite plate, the process of selecting points on radiographic markers, and process of eliminating teeth and radiographic scatter

Recording the CT image is described in more detail with reference to a flow chart, identified by the reference numeral 300, in FIG. 3. In short, FIG. 3 shows an exemplary process of imaging the patient with CT, locating three points in the CT data, and eliminating teeth and radiographic scatter. The process begins with placing or positioning the CT bite plate assembly 12 in the patient's mouth, at a step 302. Here, the bite plate assembly 12 may include the registration material for taking an impression of the patient's upper and lower teeth.

At a step 304, the patient is positioned, with the CT bite plate between his teeth, in a CT machine. The patient's head is positioned in proper diagnostic alignment to horizontal and to the imaging detector. Accordingly, the patient's head is held in a natural position, rather than an unnatural position. To position the patient's head, he or she may be instructed to look at a location, such as a mirror or point on a wall, that is disposed relatively horizontally from his or her head.

At a step 306, the patient and the CT bite plate 12 are imaged with computed tomography. If the CT bite plate 12 includes the registration material, then the diagnostic jaw position is recorded with the patient's teeth in the registration material.

At a step 308, a point on each marker is located in 3D computer space. In some exemplary embodiments, the point on the marker may be the most superior point on the surface of the marker. Other points on the marker may be used with equal success, such as for example, the lowermost point, a side location or a tip of a pointed marker.

Figures 8A, 8B:
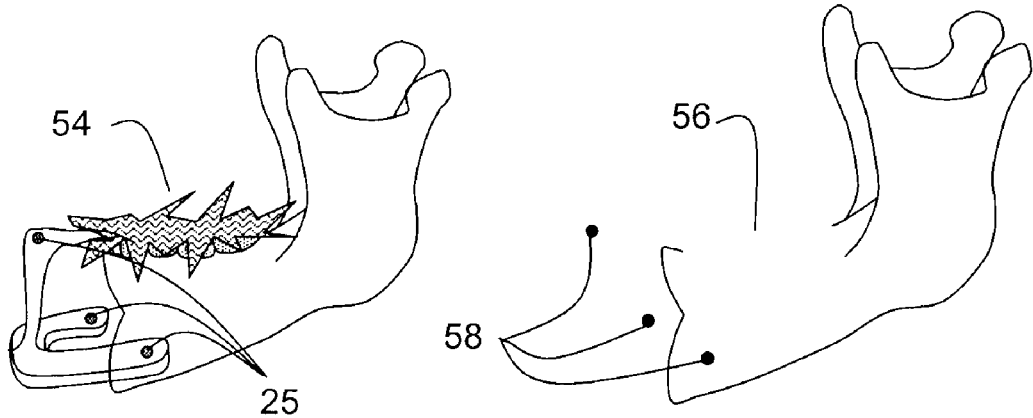
FIGS. 8A and 8B are illustrations of exemplary rendered data from CT imaging with the radiograph scatter present (as in FIG. 8A) and removed (as in FIG. 8B).

At a step 310, the collected CT data is reformatted to create a volume rendered model of the diagnostic anatomy of the patient. While the collected CT data may be used to create a full model of the diagnostic anatomy of the head and face of the patient, FIG. 8A shows one example of only a part of the full model of the diagnostic anatomy. In FIG. 8a, mandible data of the full model is shown with the three radiopaque markers 25 and with the radiographic scatter 54 due to dental fillings and crowns. This scatter makes the CT data set for the teeth non diagnostic. Returning to FIG. 3, at a step 312, the radiographic scatter is eliminated, along with the teeth from the virtual computer model. FIG. 8B illustrates the altered file with the teeth and radiographic scatter removed 56 and the radiographic markers replaced as precise points 58 located from the CT bitmap of the markers.

At a step 314, the mandible data is separated from the rest of the computer model, as is shown in FIGS. 8A and 8B, to allow for movement of the mandible independent of the rest of the computer model. This provides the ability to analyze jaw movement and develop a treatment plan consistent with desired jaw movement.

Figure 4A:
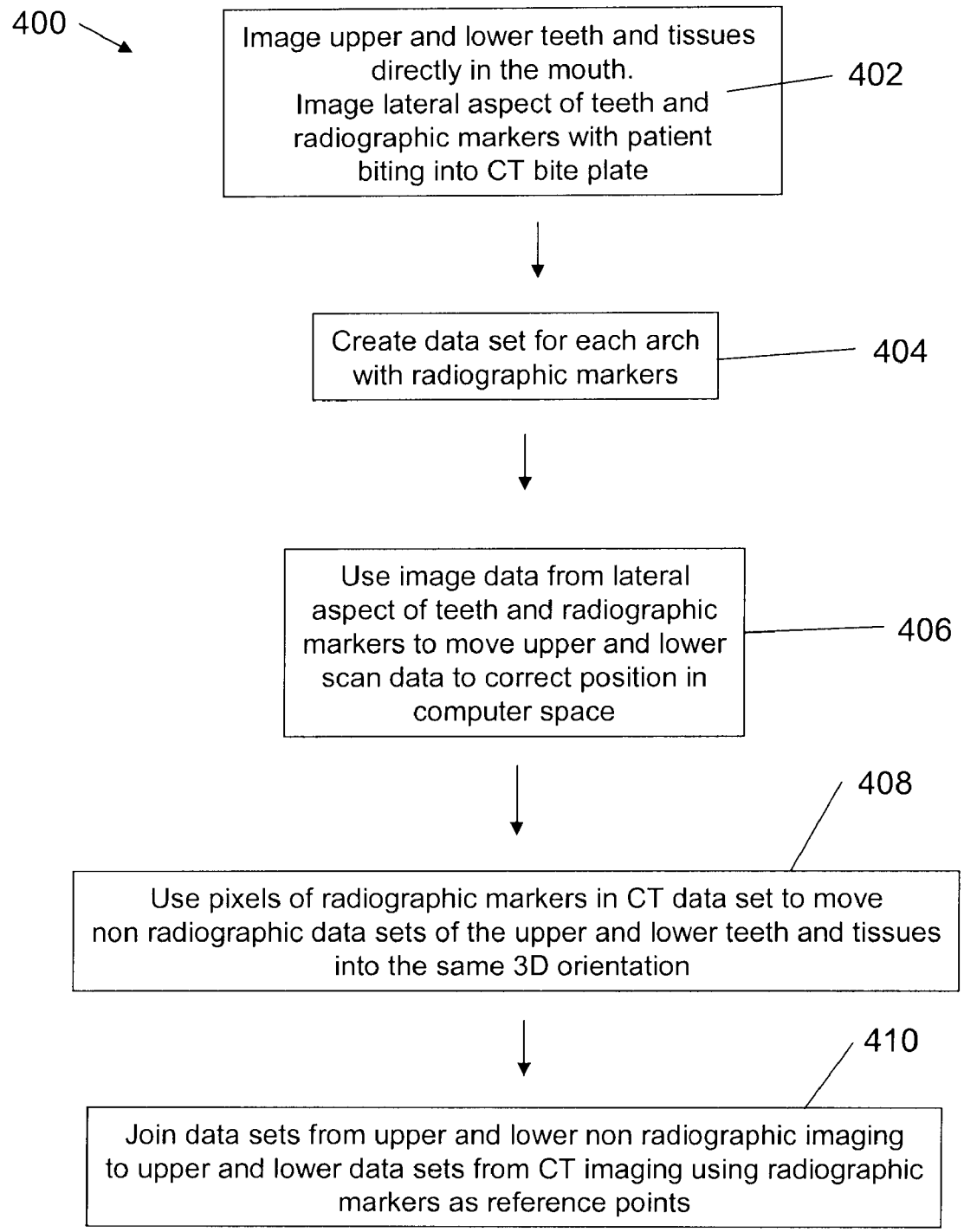
FIGS. 4A and 4B are flow charts showing exemplary processes of non-radiographic imaging of a patient's teeth and radiographic markers. Joining CT data sets with obtained non-radiographic data sets is also illustrated.
Figure 4B:
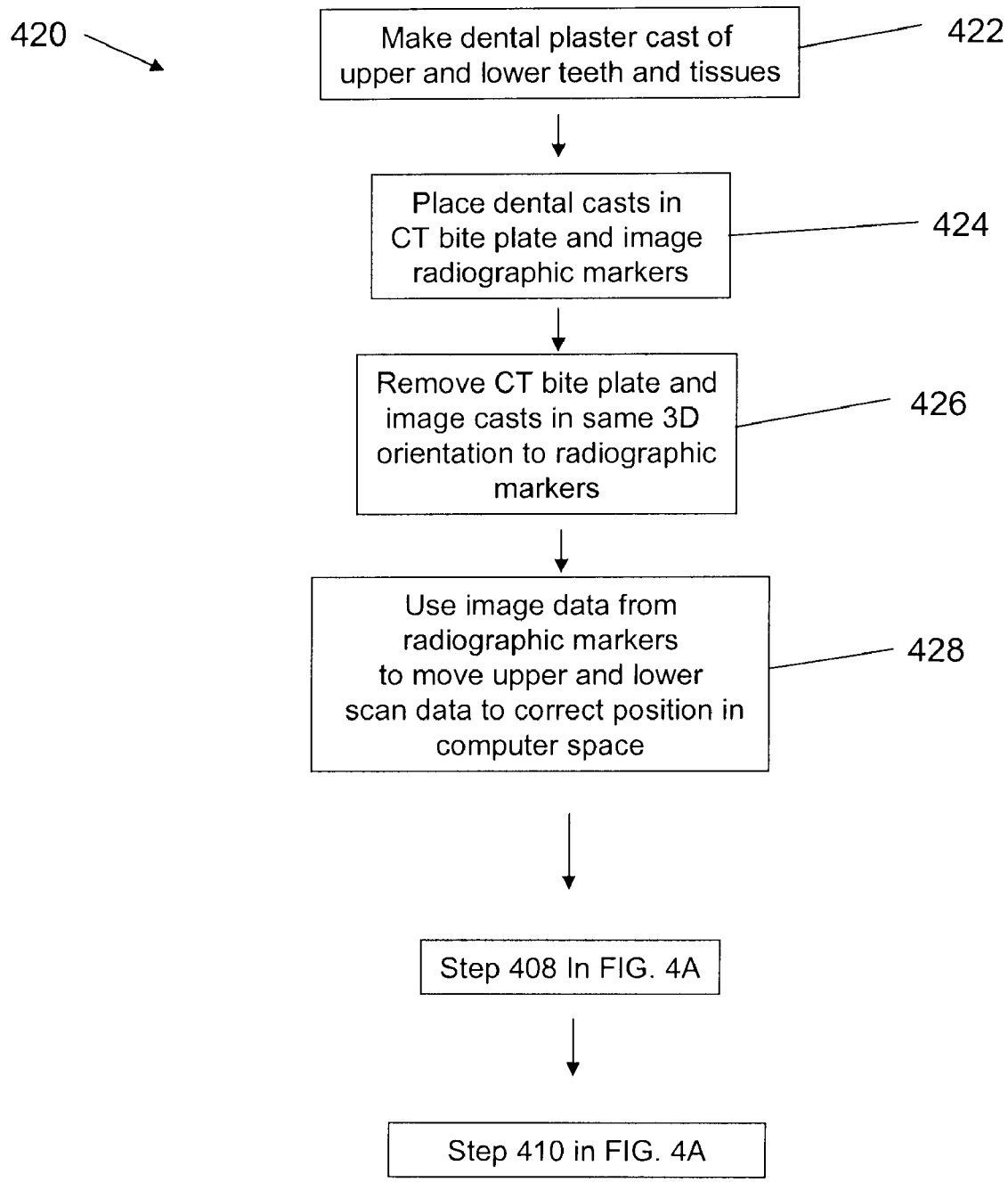

Either before or after the CT image is obtained as described in the flow chart 300, a non-radiographic image of the patient's teeth also may be obtained. FIG. 4A illustrates an exemplary process of non-radiographic imaging the patient's teeth directly in the mouth and FIG. 4B illustrates the process of imaging dental casts to create a data set of the teeth tissues and radiographic markers.

Referring first to FIG. 4A, a process for generating a non-radiographic image is shown in a flow chart, referred to by the reference numeral 400. The process begins at a step 402 by inserting the CT bite plate 12 into the patient's mouth and imaging the upper and lower teeth and tissue directly in the mouth. Also at this time an image is taken of a lateral aspect of the teeth and the radiographic markers with the patient biting into the CT bite plate. These images may be taken using non-radiographic imaging devices, such as laser devices, light devices, or holographic devices to image the teeth.

At a step 404, a data set is created for the top arch and a data set is created for the bottom arch. Each of these data sets also includes data representing the radiographic markers.

At a step 406, the image data of the lateral aspect of the teeth and of radiographic markers may then be used as a reference to move and locate the upper and lower scan data to a correct position in the computer space.

Figure 9:
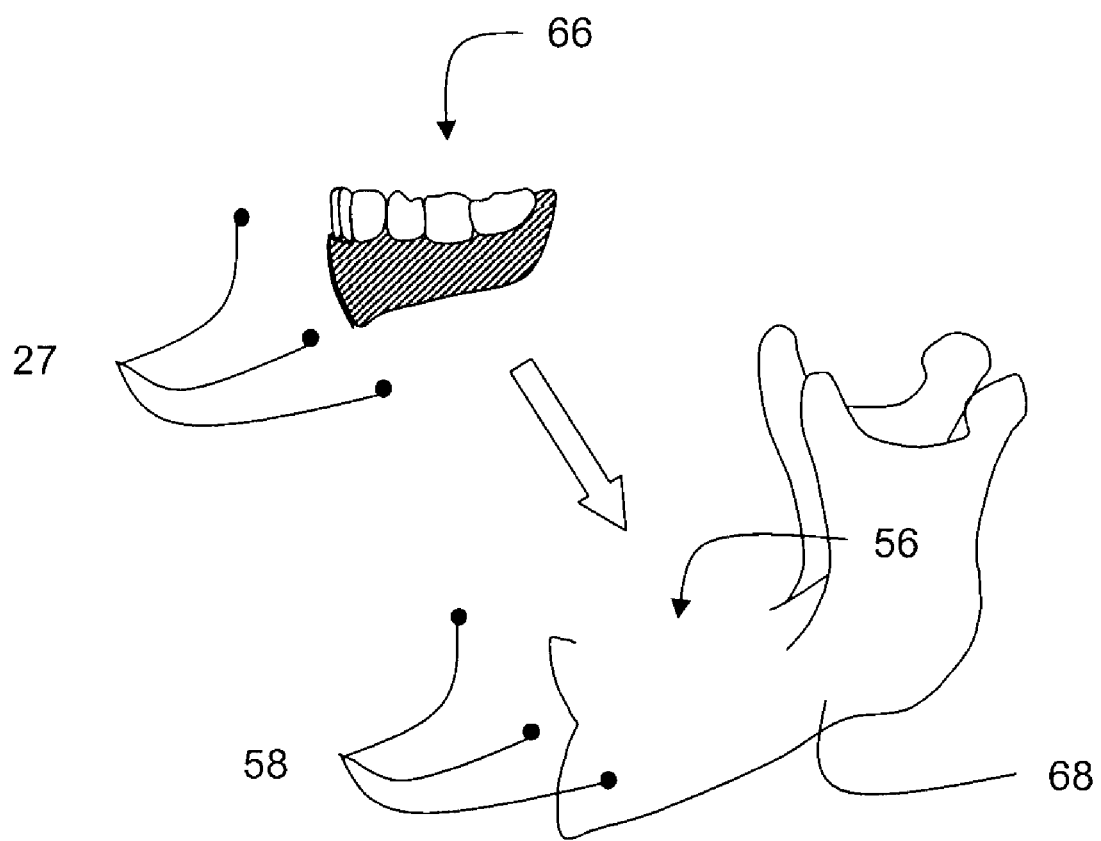
FIG. 9 illustrates exemplary non-radiographic data set of the lower teeth being joined to an exemplary CT data set of the mandible using the radiographic markers for orientation.

The CT data set and the non-radiographic data set are then brought together. At a step 408, pixels of the radiographic markers in the CT data set are used as references to move the non-radiographic data sets of the upper and lower teeth and tissues into the same 3D orientation. FIG. 9 shows one example of how this may appear, but shows only the lower teeth and jaw, with the non-radiographic imaging of the teeth 66 and the CT scan data 68.

Finally, at a step 410, the data sets from the upper and lower non-radiographic imaging are joined to the upper and lower data sets from CT imaging using the radiographic markers as reference points. Joining may be accomplished using Boolean operations and may occur for both the upper teeth set and for the lower teeth set.

Another exemplary process of capturing a non-radiographic image is described with reference to a flow chart, referenced as 420 in FIG. 4B. Here, at a step 422, a dental plaster cast is made of the upper and lower teeth and tissues. These may be made in any conventional manner.

Figure 7:
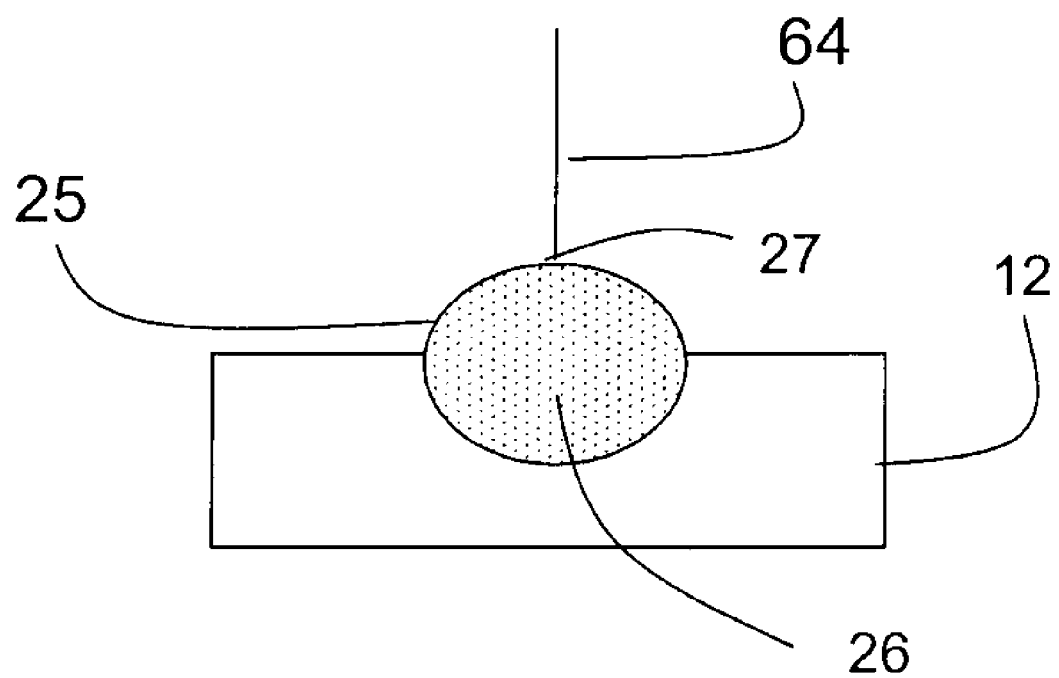
FIG. 7 is a schematic of an exemplary radiographic marker.

At a step 424, the dental casts are placed in the CT bite plate 12 and the radiographic markers are imaged by a scanning machine. One example of this is shown in FIG. 6, where the lower cast is shown with the CT bite plate. Here, the radiographic markers are being imaged by a contact digitizer. A closer view is shown in FIG. 7, where a specific point on the marker 25 may be digitized for later reference.

At a step 426, the CT bite plate is removed and the upper and lower casts are imaged in the same 3D orientation as was the radiographic markers. Accordingly, the dental casts are imaged relative to the radiographic markers in the CT bite plate 12. Once one of the upper and lower casts is imaged, the other also may be imaged. Separate imaging of the upper and lower casts enables easier analysis for treatment, as described further below.

At a step 428, image data from the radiographic markers may be used to orient the scan data of the upper and lower casts and move them to correct positions in the computer space. Then, at step 408, as described above with reference to FIG. 4A, pixels of radiographic markers in the CT data set are used as reference points to move and orient the non-radiographic data sets of the upper and lower teeth and tissues into the same 3D orientation. At step 410, the data sets from the upper and lower non-radiographic imaging are joined to the upper and lower data sets from CT imaging using the radiographic markers as reference points.

FIG. 5 illustrates an exemplary upper dental cast 40 and an exemplary lower dental cast 41 positioned into the CT bite plate 12 to reproduce the precise jaw position made in the CT scan. The cast holder 45 is a mechanical device that has an upper member 32 and lower member 34 that can be separated and repositioned into the exact same orientation. Each cast is also joined to a mounting plate 49 that precisely connects to the upper and lower member of the cast holder with a mechanical or magnetic receiver 60. After mounting the casts in the cast holder, the upper and lower dental casts can be removed and placed in the imaging system. The digital imaging system can use any number of methods that include laser, light, holographic or contact digitizing to image the dental casts and the CT bite plate.

FIG. 6 illustrates one exemplary embodiment using contact digitizing to create a data set of the lower cast with and without the CT bite plate and the upper cast. The CT bite plate and the lower cast are moved to the scanner 62 from the cast holder and the cast and CT bite plate are positioned in the receiver 60 and scanned. The probe of the scanner 64 creates a data set of the surface of the CT bite plate on the lower cast. The contours of the radiographic markers are scanned with the probe and the precise location of the markers recorded in three-dimensional computer space. A second scan is made of the lower cast with the CT bite plate removed from the cast, thereby providing an accurate digital data set for an image of the lower cast. Finally, the upper cast is placed in the receiver 60 and scanned. Since the orientation of the upper cast relative to the lower cast is known and reproduced with the cast holder 45 it is possible to move the data set for the upper cast in three-dimensional computer space to the exact relationship that existed when the casts were mounted in the cast holder In some examples, the upper and lower casts are placed within the scanner in a fully occluded position, not separated by the CT bite plate. In this position, the upper and lower casts are scanned together. The CT bite plate may then be inserted between the upper and lower casts, and then may be imaged to measure the separation generated by the CT bite plate. Thus, the second scan will correspond in separation distance to the full CT image, including the CT bite plate.

FIG. 7 illustrates a radiographic marker with a specific geometric shape that can be scanned easily with the contact digitizer. As shown in FIG. 7, in some embodiments, the radiographic markers 25 may be disposed on and protrude from the surface of the CT bite plate 12. One example is a sphere 26 that is attached to the CT bite plate 12. The probe from the contact digitizer records a data set for the exposed surface of the spherical radiographic marker and a specific point with an x, y, and z location can be recorded 27. A useful example is the most superior point on the surface of the sphere. The same point can be located on the data set from the CT scan of the patient. This data will be represented as grayscale bitmaps. The pixel that represents the most superior pixel on the radiographic image can also be easily located and recorded. By locating three non-linear points on markers in the CT data as well as the contact digitizing data it is possible to move the data sets for the upper and lower cast into the same orientation as existed for the CT scan data. This creates a virtual model of the CT data as well as the contact digitizing data in the same three-dimensional computer space.

The CT data set is then reformatted as a 3D computer model such as a stereolithography (.stl) image or any number of 3D computer renderings. FIG. 8A illustrates the reformatted scan data from CT imaging with the three radiopaque markers 25 and radiographic scatter 54 due to dental fillings and crowns. This scatter makes the CT data set for the teeth non diagnostic. FIG. 8B illustrates a portion of the altered .stl file with the teeth and radiographic scatter removed 56, as described in FIG. 3, and the radiographic markers replaced as precise points 58 located from the CT bitmap of the markers.

FIG. 9 illustrates the scan data from non-radiographic imaging of the teeth 66. Three points 27 indicate the position of the markers in the scan data. The CT scan data 68 with points representing the radiographic markers 58 are illustrated with the radiographic scatter removed 56. It is then possible to move the computer data representing the teeth 66 to its correct spatial position in relation to the CT data 68 using a three point move from the points recording the marker positions 27 to the computer position represented in the CT scan indicated by points 58. Once moved, the radiographic and non-radiographic data can be joined using Boolean operations. The same process can be used to move the scan data of the upper teeth into proper position the CT scan data.

Figure 10:
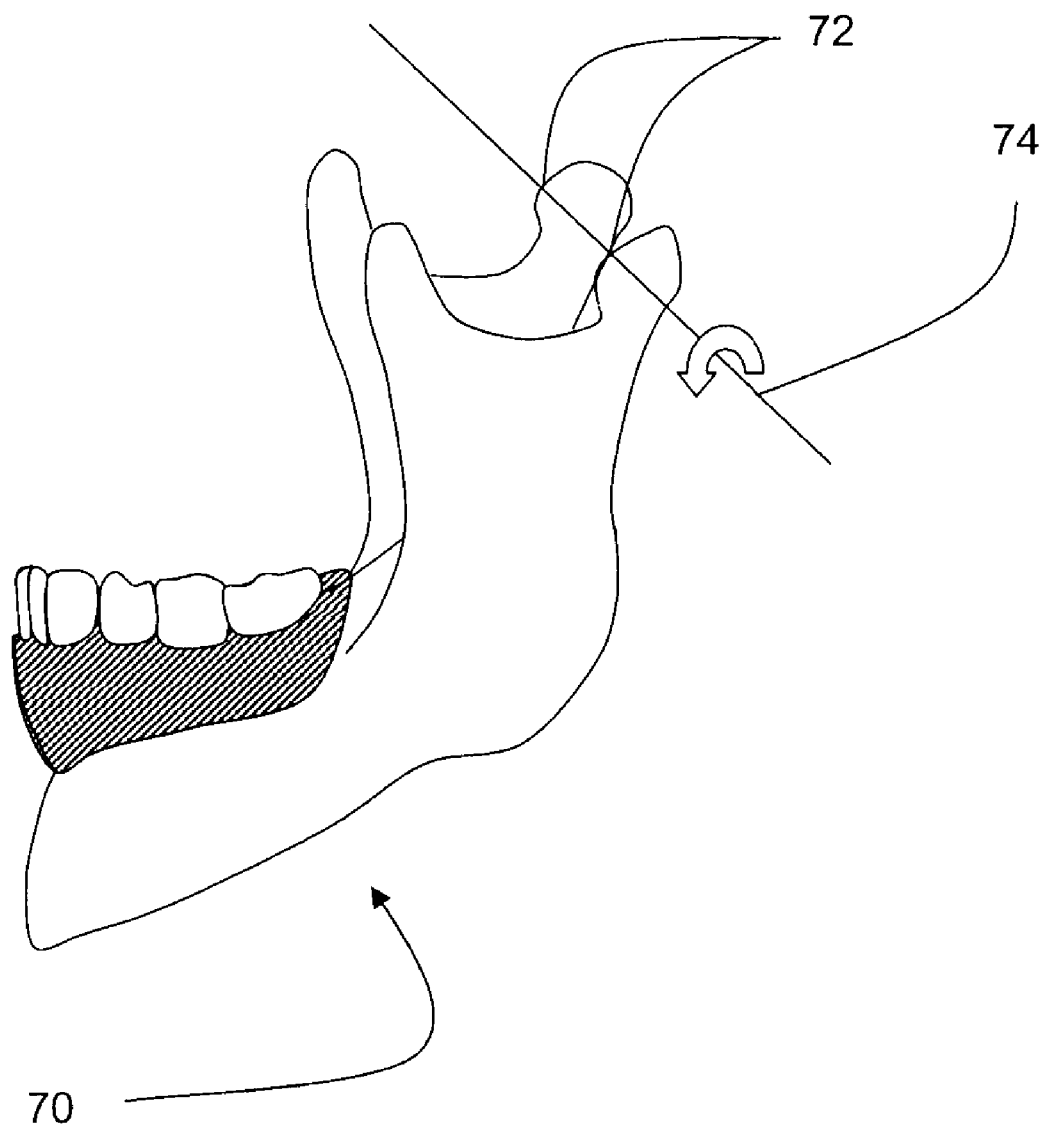
FIG. 10 is a schematic of an exemplary perfected virtual model and the axis of rotation for the lower jaw.

Referring to FIG. 10 the perfected model 70 is illustrated with non-radiographic data from the teeth joined to CT data of the mandible, which was separated from the rest of the scanned data in step 314 of FIG. 3. Points can be selected on or in the area around the articulating surfaces of the condyles 72 to represent the rotational center 74 for the mandible. In a conventional system for determining rotational center, the patient's ear holes are used with a face bow to determine an approximation of the position of the rotational centers. This improved method eliminates the need for a face bow, and the system can determine an approximation for the position of the rotational center. Movement of the mandibular computer model can also be controlled by using standard condylar inclinations and Bennett angles to define average movements.

Figure 11A:
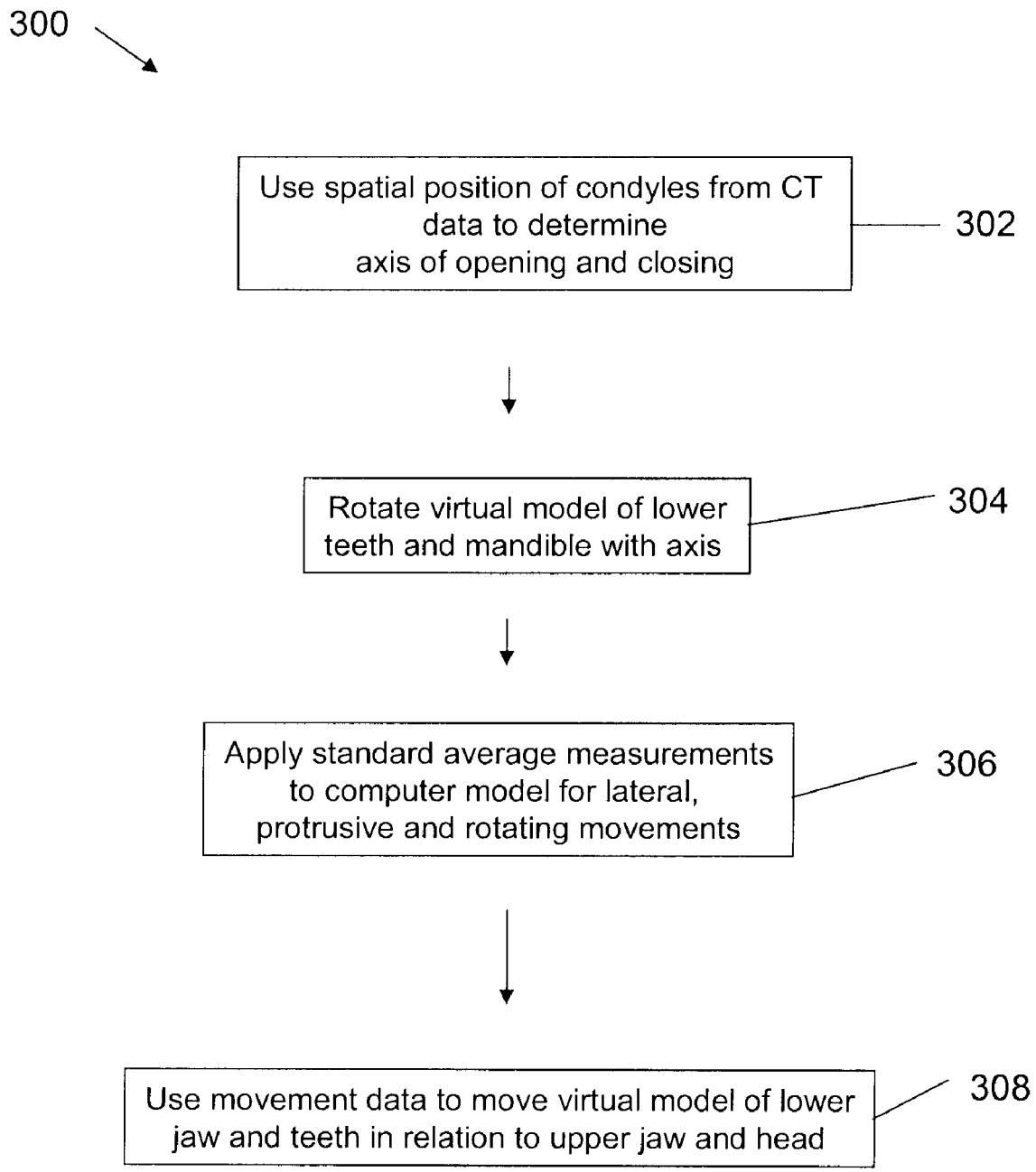
FIGS. 11A and 11B are flow charts showing exemplary processes for creating movement for the lower jaw in a virtual model.
Figure 11B:
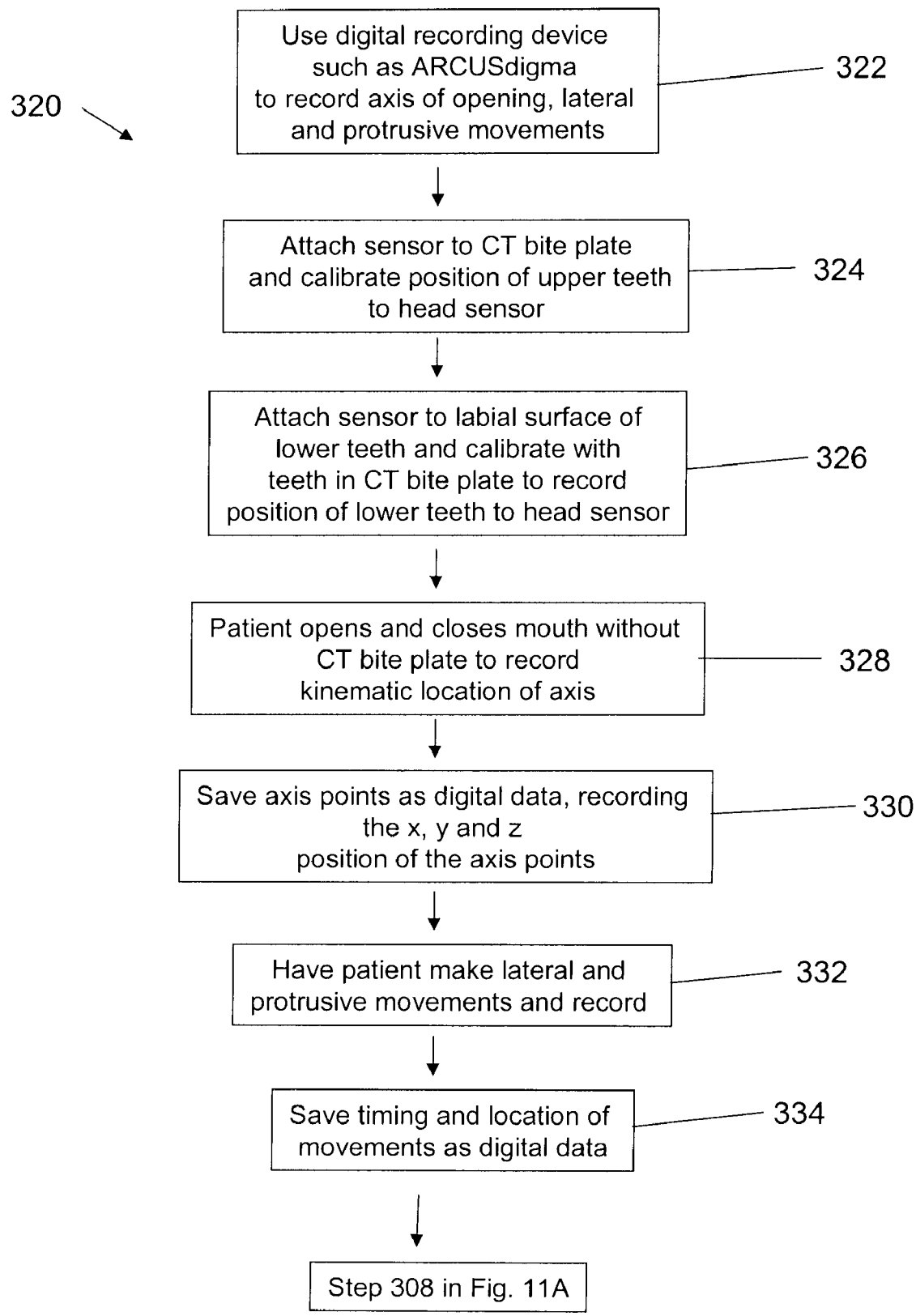

FIGS. 11A and 11B illustrate exemplary processes in a flow chart, referenced herein as 300 and 320 respectively, for applying movement to the mandibular computer model so that the rotational center can be determined.

FIG. 11A begins at a step 302 of using spatial position of condyles from the CT data to determine an axis of opening and closing. This axis may be determined by selecting points on or in the area around the condyles 72 to represent the rotational center 74 for the mandible, as described above with reference to FIG. 10. This may be done with a conventional input device, such as a keyboard, mouse, or other input device. Because the CT data contains all the information for the mandible and condyles, selecting points on or in the area around the condyles 72 may identify the rotational center more accurately than prior art devices relying on the face bow.

At a step 304, a user rotates the virtual model of the lower teeth and the mandible about the axis. Using methods known the art, at a step 306, the user may then apply standard average measurements to computer model for lateral, protrusive and rotating movements to obtain calculated movement data. At a step 308, the obtained movement data is used to move the virtual model of lower jaw and teeth in relation to the upper jaw and head.

In an alternative embodiment, instead of estimating and selecting the rotational axis, the rotational axis is determined through additional scanning steps. One example of this process is shown in and described relative to FIG. 11B. This process may begin at a step 322, where a digital recording device, such as, for example ARCUSdigma, records the axis of opening, lateral, and protrusive movements of the mandible. At a step 324, at least one sensor is associated with the CT bite plate and calibrated to identify the position of the upper teeth relative to a head sensor. This is represented and described with reference to FIG. 12 below.

At a step 326, the sensor attaches to the labial surface of lower teeth and calibrates with teeth in the CT bite plate to record the position of the lower teeth relative to the head sensor. At a step 328, the CT bite plate may be removed, and the patient opens and closes his mouth to record the kinematic location of axis. At a step 330, the axis points are saved as digital data, such as for example, as ASCI Text, thereby recording the x, y and z position of the axis points.

At a step 332, the patient moves the mandible laterally and protrusively, and the relative location, as determined by the sensors, is recorded.

At a step 334, the timing and location of movements are saved or stored as digital data, such as the ASCI Text. Then, as described above with reference to FIG. 11A, the movement data may be used to move the virtual model of the lower jaw and teeth in relation to the upper jaw and the head.

Figure 12:
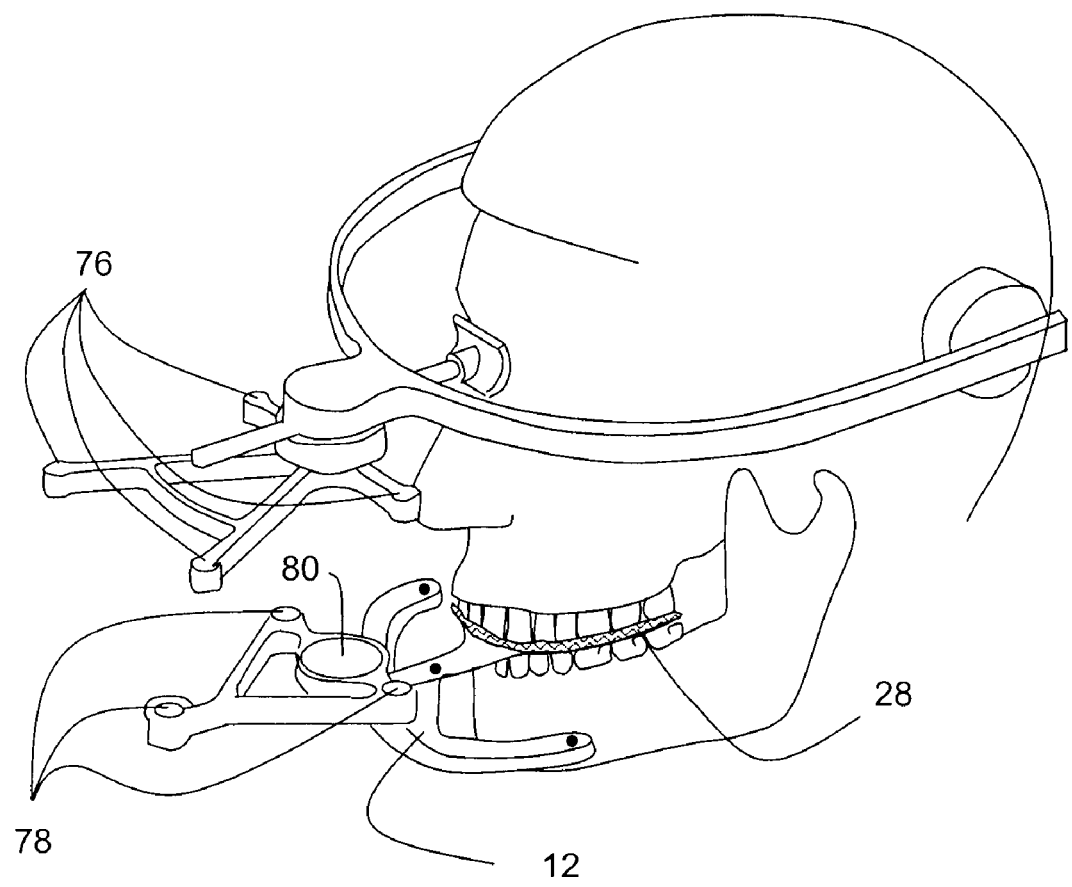
FIG. 12 is a schematic diagram of an exemplary digital recorder attached to the CT bite plate.

FIG. 12 illustrates an exemplary process and system for applying movement to the mandibular computer model. Positional tracking of the patient's physical mandible can be accomplished in many ways that include ultrasound, infrared, light and other methods of recording the positional relationship of the maxillae and mandible to a sensor. The ARCUSdigma (KaVo Company) digital recorder is ideally suited for this task. Four ultrasound microphones 76 are attached to the head and three ultrasonic transmitters 78 are attached to the CT bite plate with a magnetic fixation device 80. The patient bites into the bite registration 28 to reproduce the same positional relationship existed when the CT scan was made. The ARCUSdigma is then calibrated using the operational software. This first calibration records the position of the ultrasonic transmitters 78, CT bite plate 12, and upper teeth in relation to the microphones 76.

Figure 13:
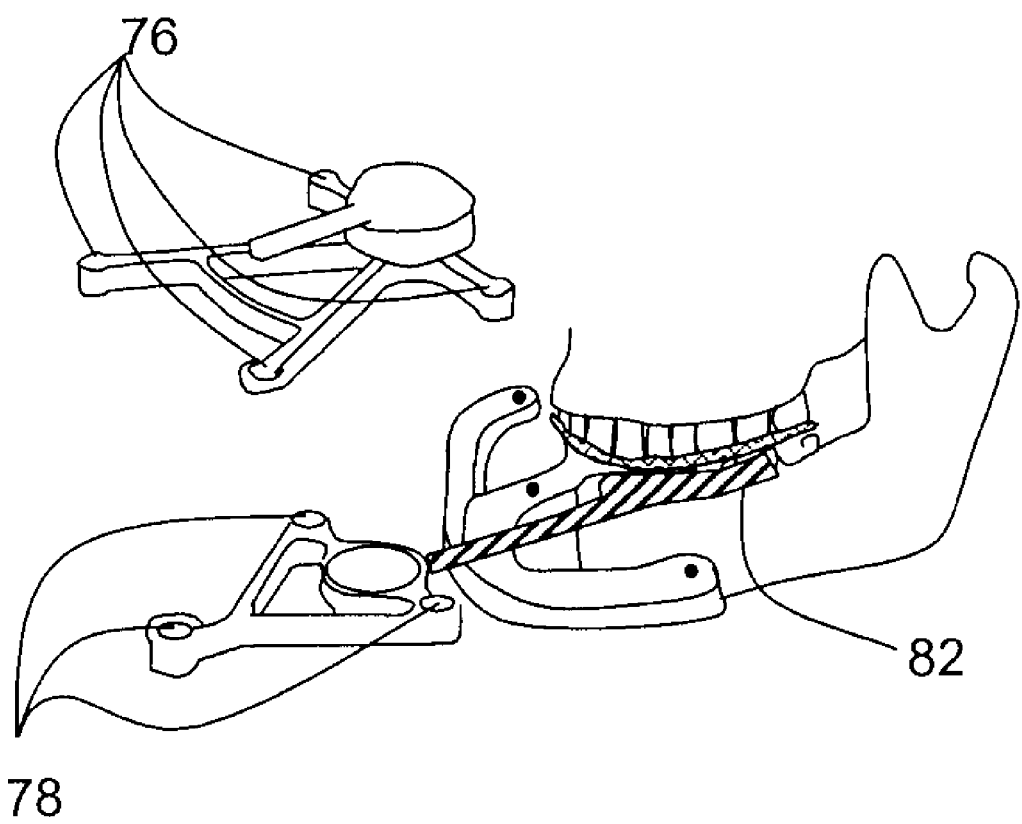
FIG. 13 is a schematic diagram of the exemplary digital recorder attached to the lower bite fork.

FIG. 13 illustrates the lower bite fork 82 attached to the lower teeth such that it is rigidly connected to the teeth and gums and yet below the CT bite plate. The ultrasonic transmitters 78 are then attached to the lower bite fork and the software again is calibrated to record the positional relationship of the lower bite fork and transmitters to the microphones 76 with the patient's teeth in the CT bite plate. The CT bite plate can then be removed to record the motion of the lower jaw to the upper.

Figure 14:
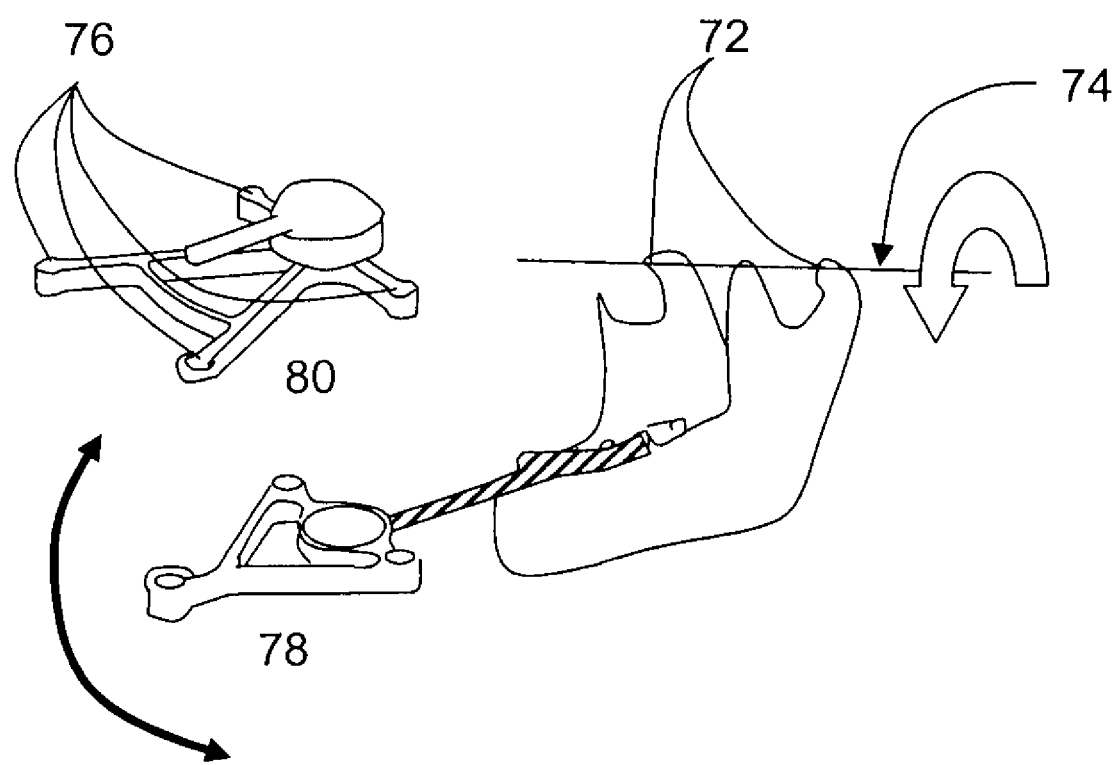
FIG. 14 is an illustration of movement of an exemplary lower jaw to record and locate the axis of rotation of the lower jaw.

FIG. 14 illustrates the process for locating the actual rotational axis of the mandible. The patient's lower jaw is guided in opening and closing positions. The software can then calculate the actual position of the condylar rotational points 72 on the axis of rotation 74. This information is recorded as digital data, such as ASCI Text, and can be directly related to the virtual jaw model described in this invention. The patient can then move in protrusive and right and left lateral jaw movements. The software will record the timing and positional movement of the jaw and record the data as digital data, such as ASCI Text. This text can then be used to move the virtual model of the mandible in computer space.

Figure 15:
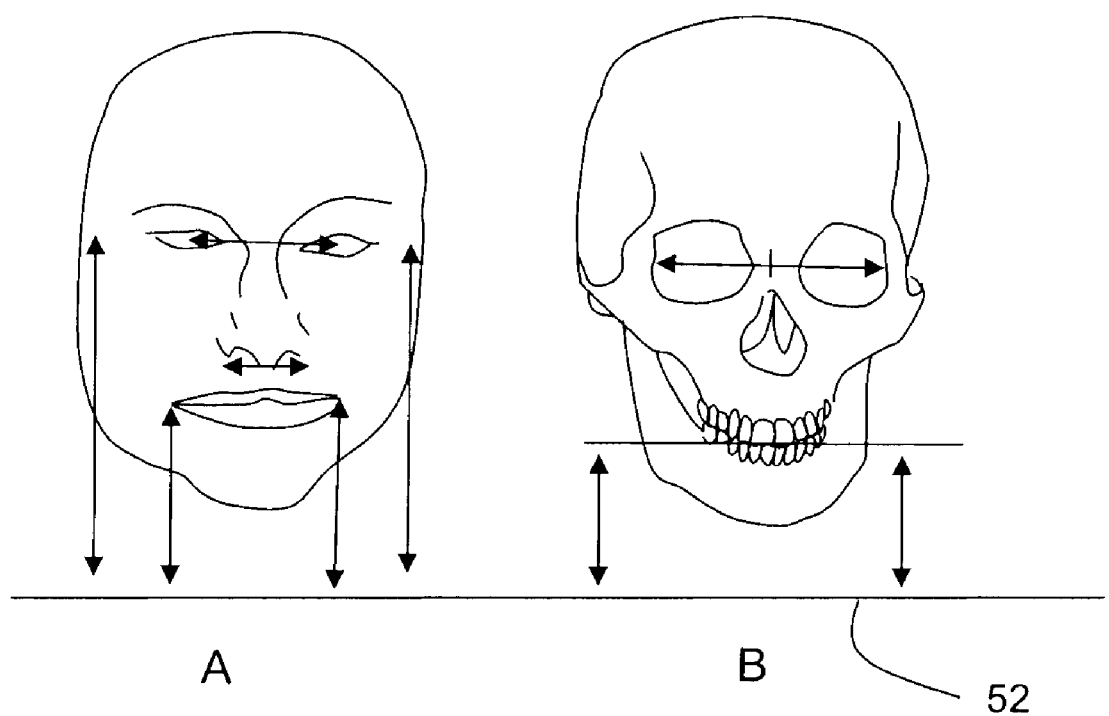
FIGS. 15A and 15B are illustrations of an exemplary virtual model with soft and hard tissues rendered in relation to the horizontal plane.

FIG. 15 illustrates the perfected model used to evaluate the aesthetic position of soft and hard tissues in a natural position, and in relation to the horizontal edge of the sensor 52. Pixels with a grayscale value to render soft tissue (FIG. 15A) can be selected to produce a computer model of the face, nose, ears, and many other structures on the surface of the head. Pixels with a grayscale value for bone and teeth can also be selected to render a computer model (FIG. 15B) in the same orientation.

Figure 16:
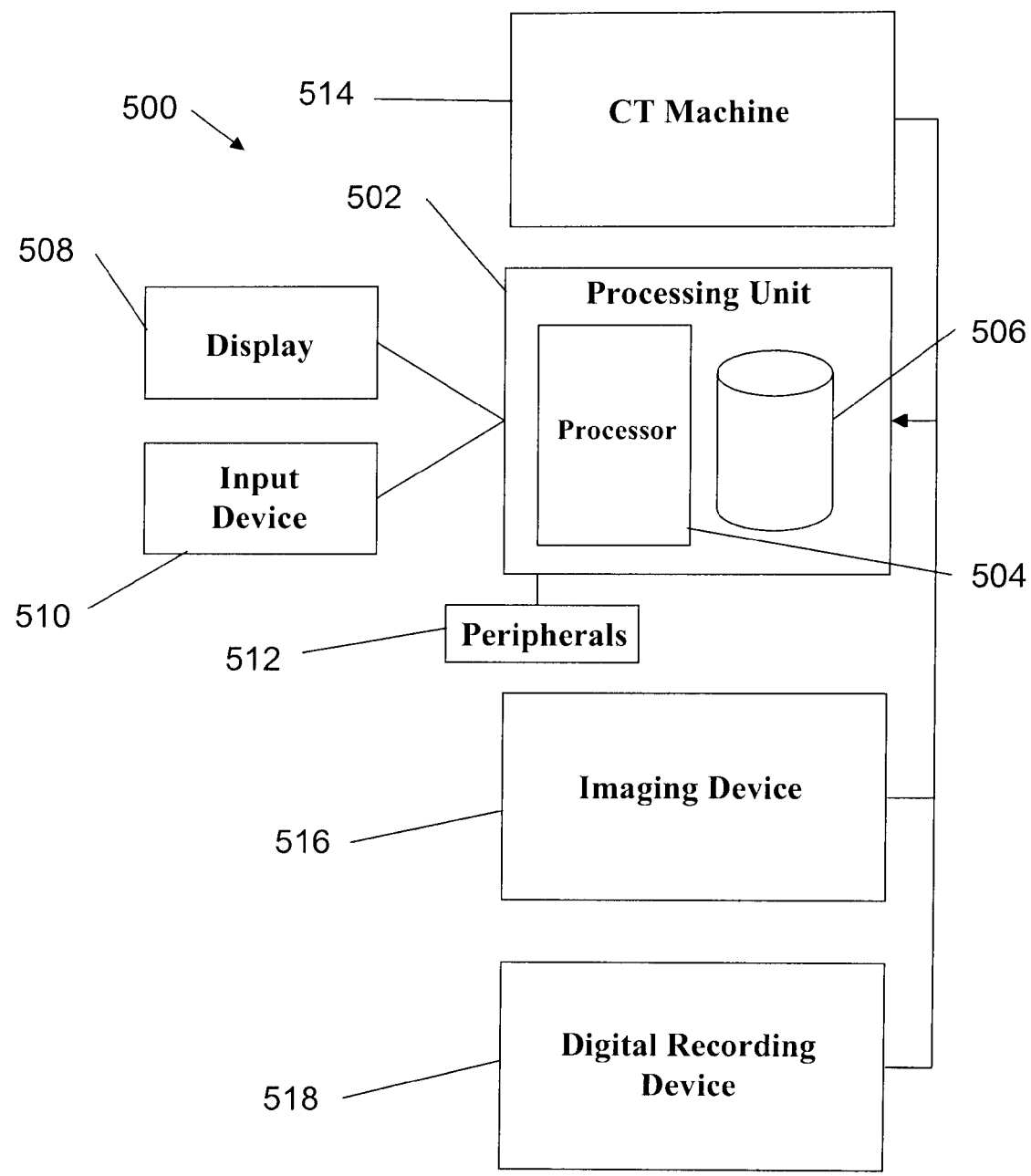
FIG. 16 is a block diagram of an exemplary system usable to accomplish the methods disclosed herein.

An exemplary system for performing the processes and methods described herein is shown in FIG. 16. FIG. 16 includes a computer system 500 including a processing unit 502 containing a processor 504 and a memory 506. An output device, such as a display 508 and input devices 510, such as keyboards, scanners, and others, are in communication with the processing unit 502. Additional peripheral devices 512 also may be present.

The processor 504 may for example be a microprocessor of a known type. The memory 506 may, in some embodiments, collectively represents two or more different types of memory. For example, the memory 506 may include a read only memory (ROM) that stores a program executed by the processor 504, as well as static data for the processor 504. In addition, the memory 506 may include some random access memory (RAM) that is used by the processor 504 to store data that changes dynamically during program execution. The processor 504 and the memory 506 could optionally be implemented as respective portions of a known device that is commonly referred to as a microcontroller. The memory 506 may contain one or more executable programs to carry out the methods contained herein, including joining, separating, storing, and other actions including Boolean actions.

The system 500 also may include a CT machine 514, an imaging device 516, and a digital recorder 518. These may be any of the CT machines, imaging devices, and digital recorders described herein. Data from the CT machine 514, the imaging device 516, and the digital recorder 518 may be accessed by the processing unit 502 and used to carry out the processes and methods disclosed. Data may be communicated to the processing unit 502 by any known method, including by direct communication, by storing and physically delivering, such as using a removable disc, removable drive, or other removable storage device, over e-mail, or using other known transfer systems over a network, such as a LAN or WAN, including over the internet or otherwise. Any data received at the processing unit 502 may be stored in the memory 506 for processing and manipulation by the processor 504. In some embodiments, the memory 506 is a storage database separate from the processor 504. Other systems also are contemplated.

While embodiments of the invention have been illustrated and described in detail in the disclosure, the disclosure is to be considered as illustrative and not restrictive in character. All changes and modifications that come within the spirit of the invention are to be considered within the scope of the disclosure.

I claim:

1. A dental apparatus, comprising:
    a bite registration section formed of a radiolucent material and being configured to fit within a patient's mouth and mate with the patient's teeth;
    a central forward projection extending from the bite registration section configured to extend between lips when the bite registration section is in the mouth;
    an exterior portion configured to reside outside the mouth, the exterior portion being attached to the central forward projection, the exterior portion having a central vertical portion extending downward from the central forward projection, a first wing extending laterally from the central vertical portion in a first direction, and a second wing extending laterally from the central vertical portion in a second direction, the first and second wings being below the bite registration section; and
    at least three non-linear radiographic markers disposed on the exterior portion and having a radiographic density that makes them visible in CT data, at least one of said markers being disposed on said central vertical portion, at least one of said markers being disposed on said first wing, and at least one of said markers being disposed on said second wing.

2. The dental apparatus of claim 1 wherein said exterior portion comprises at least one wing configured to follow a contour of the patient's face.

3. The dental apparatus of claim 1 wherein said bite registration section comprises a U-shaped section.

4. The dental apparatus of claim 1 wherein at least one of said at least three non-linear radiographic markers is configured to reside above a plane of occlusion of the patient's teeth.

5. The dental apparatus of claim 1 wherein at least one of said at least three non-linear radiographic markers is configured to reside below a plane of occlusion of the patient's teeth.

6. The dental apparatus of claim 1 wherein said apparatus is formed entirely of a substantially radiolucent material except for said at least three non-linear radiographic markers.

7. A dental apparatus, comprising:
a radiolucent bite registration section configured to fit within a patient's mouth and mate with the patient's teeth;
said bite registration section comprising impressions of the patient's upper and lower teeth;
a forward projection extending from said bite registration section, said forward projection being configured to extend outside the patient's mouth when said bite registration section is in the patient's mouth;
an exterior portion depending from said forward projection, said exterior portion being configured to reside outside the patient's mouth and having a pair of wings extending laterally from a vertical portion below said bite registration section such that said pair of wings is disposed proximal to the patient's chin; and
a plurality of radiographic markers disposed on said pair of wings and configured to reside below a plane of occlusion of the patient's teeth.

8. The dental apparatus of claim 7 wherein said pair of wings comprises a curved shape that extends laterally along both sides of the patient's face and has a lateral span that is less than the width of the patient's face.

* * * * *